(12) United States Patent
Liu et al.

(10) Patent No.: US 7,342,021 B2
(45) Date of Patent: Mar. 11, 2008

(54) PHOSPHODIESTERASE 4 INHIBITORS

(75) Inventors: Ruiping Liu, Huntington, NY (US);
Hans-Jurgen Ernst Hess, Old Lyme, CT (US); Allen Hopper, Glen Rock, NJ (US); Ashok Tehim, Ridgewood, NJ (US); Yajing Rong, Monmouth Junction, NJ (US)

(73) Assignee: Memory Pharmaceuticals Corp., Montvale, NJ (US)

( * ) Notice: Subject to any disclaimer, the term of this patent is extended or adjusted under 35 U.S.C. 154(b) by 0 days.

(21) Appl. No.: 10/067,996

(22) Filed: Feb. 8, 2002

(65) Prior Publication Data

US 2003/0045533 A1    Mar. 6, 2003

Related U.S. Application Data

(60) Provisional application No. 60/344,824, filed on Jan. 7, 2002, provisional application No. 60/267,195, filed on Feb. 8, 2001.

(51) Int. Cl.
*C07D 473/34* (2006.01)
*A61K 31/52* (2006.01)
*A61P 37/08* (2006.01)
*A61P 25/28* (2006.01)
*A61P 29/00* (2006.01)

(52) U.S. Cl. .................... 514/263.4; 544/277
(58) Field of Classification Search ............... 544/277, 544/276; 514/263.4, 263.2, 263.37
See application file for complete search history.

(56) References Cited

U.S. PATENT DOCUMENTS

| | | | |
|---|---|---|---|
| 3,917,563 A | 11/1975 | Meyer et al. | |
| 3,919,192 A | 11/1975 | Meyer et al. | |
| 5,013,829 A | 5/1991 | Nair et al. | |
| 5,073,559 A | 12/1991 | Coates | |
| 5,525,606 A | 6/1996 | Moschel et al. | |
| 5,744,473 A | 4/1998 | Chasin et al. | |
| 5,814,651 A | 9/1998 | Duplantier et al. | |
| 5,864,037 A | 1/1999 | Chasin et al. | |
| 5,935,978 A | 8/1999 | Fenton et al. | |
| 5,939,422 A | 8/1999 | Cavalla et al. | |
| 6,037,470 A | 3/2000 | Cavalla et al. | |
| 6,040,447 A | 3/2000 | Cavalla et al. | |
| 6,057,445 A | 5/2000 | Cavalla et al. | |
| 6,211,367 B1 | 4/2001 | Cavalla et al. | |
| 6,228,859 B1 | 5/2001 | Cavalla et al. | |
| 6,310,205 B1 | 10/2001 | Chasin et al. | |
| 6,316,928 B1 | 11/2001 | Chasin et al. | |
| 2003/0045533 A1 | 3/2003 | Liu et al. | |
| 2004/0102460 A1 | 5/2004 | Hopper et al. | |
| 2006/0052331 A1* | 3/2006 | Koch et al. | 514/45 |
| 2007/0093510 A1* | 4/2007 | Tehim et al. | 514/263.2 |

FOREIGN PATENT DOCUMENTS

| | | |
|---|---|---|
| DE | 2 405 895 | 8/1974 |
| DE | 42 30 755 | 3/1994 |
| DE | 197 02 785 | 7/1998 |
| DE | 199 35 209 | 2/2001 |
| EP | 1 043 324 | 10/2000 |
| JP | 62-10085 | 1/1987 |
| JP | 62-240622 | 10/1987 |
| JP | 05-001066 | 1/1993 |
| JP | 10-72415 | 3/1998 |
| JP | 11-180982 | 7/1999 |
| JP | 11-189577 | 7/1999 |
| JP | 2000-72773 | 3/2000 |
| JP | 20000-72773 | 3/2000 |
| WO | WO 93/25517 | 12/1993 |
| WO | WO 94/14742 | 7/1994 |
| WO | WO 98/58901 | 12/1998 |
| WO | WO99/24432 | 5/1999 |
| WO | WO 99/29694 | 6/1999 |
| WO | WO 01/87281 | 11/2001 |
| WO | WO 02/098878 | 12/2002 |

OTHER PUBLICATIONS

Chalmers (TiPS vol. 17, pp. 166-172 Apr. 1996).*
"Hydroxamic acids" <http://www.iupac.org/goldbook/H02911.pdf> downloaded from the internet Jun. 30, 2006.*
Grant & Hackh's Chemical dictionary, 5th edition, pp. 115, 220 (1987).*
Thomas C. McKenzie et al., "The Gomberg-Bachmann Reaction of Purines", *J. Heterocyclic Chem.*, May-Jun. 1987, pp. 859-861, vol. 24.
Vasu Nair et al., "Novel, Stable Congeners of Antiretroviral Compound 2', 3'-Dideoxyadenosine," *J. Am. Chem. Soc.*, 1989, pp. 8502-8504, vol. 111.
James E. Kelley et al., "Antirhinovirus structure-activity relationships of 6-substituted-9-(4-methybenzyl)-2-trifluoromethyl-9H-purines," *Eur. J. Med. Chem.*, 1990, pp. 131-135, vol. 25.
Jean-Jacques Bourguignon et al., "9-Benzyladenines: Potent and Selective cAMP Phosphodiesterase Inhibitors," *J. Med. Chem*, 1997, pp. 1768-1770, vol. 40.

(Continued)

*Primary Examiner*—Mark L. Berch
(74) *Attorney, Agent, or Firm*—Millen, White, Zelano, Branigan, P.C.

(57) ABSTRACT

PDE4 inhibition is achieved by novel compounds of the Formula I:

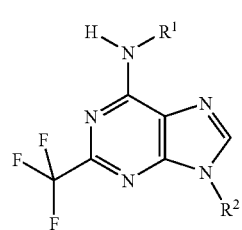

wherein $R^1$ and $R^2$ are as defined herein.

68 Claims, No Drawings

OTHER PUBLICATIONS

James L. Kelley et al., "6-(Alkylamino)-9-alkylpurines. A New Class of Potential Antipsychotic Agents," *J. Med. Chem.*, 1997, pp. 3207-3216, vol. 40.

Elisabeth Boichot et al., "Anti-Inflammatory Activities of a New Series of Selective Phosphodiesterase 4 Inhibitors Derived from 9-Benzyladenine," *The Journal Of Pharmacology And Experimental Therapeutics*, 2000, pp. 647-653, vol. 292, No. 2.

V. Vair, "Hydrolysis of Dideoxgenated Purine Nucleosides: Effect of Modification o f the Base Moiety", *J. Org. Chem*, 1990, pp. 3695-3697, vol. 55, No. 11.

H. Nagano et al., "Fluorine-Containing Potential Anticancer agents. II. Syntheses Trifuoromethylpurines and Trifluormethylthiazolopyrimidines", *J. Med. Chem.*, 1964, pp. 215-220, vol. 7, No. 2.

Vasu Nair et al., "Inhibition of mammalian adenosine deaminase by novel functionalized 2', 3'-dideoxyadenosines", *Biochim. Biophys. Acta.* 1991, pp. 121-123, vol. 1078, No. 1.

Patent Abstracts of Japan, vol. 2000, No. 6, Sep. 22, 2000, JP 200 072773, Mar. 7, 2000.

Patent Abstracts of Japan, vol. 1999, No. 12, Oct. 29, 1999, JP 11 180982, Jul. 6, 1999.

Thomas C. McKenzie et al., "The Gomberg-Bachmann Reaction of Purines", *J. Heterocyclic Chem.*, May-Jun. 1987, pp. 859-861, vol. 24.

Vasu Nair et al., "Novel, Stable Congeners of Antiretroviral Compound 2', 3'-Dideoxyadenosine," *J. Am. Chem. Soc.*, 1989, pp. 8502-8504, vol. 111.

Vasu Nair et al., "Synthesis Of Congeners Of Adenosine Resistant To Deamination by Adenosine Deaminase," *J. Chem. Soc Comm.*, 1989, pp. 876-879.

James L. Kelley et al., "Synthesis and Strcuture-Activity Relationships of 2-Substituted-6-(dimethylamino)-9-(4-methylbenzyl)-9H-purines with Antirhinovirus Activity," *J. Med. Chem.*, 1989, pp. 218-224, vol. 32.

James E. Kelley et al., "Antirhinovirus structure-activity relationships of 6-substituted-9-(4-methylbenzyl)-2-trifuloromethyl-9H-purines," *Eur. J. Med. Chem.*, 1990, pp. 131-135, vol. 25.

Roger J. Schilling et al., "A High-Throughput Assay For Cyclic Nucleotide Phosphodiesterases," *Analytical Biochemistry*, 1994, pp. 154-158, vol. 215.

Donald V. Daniels et al., "A Semiautomated Method for the Assay of Cyclic Adenosine 5'-Monophosphate Phosphodiesterase," *Analytical Biochemistry*, 1998, pp. 367-389, vol. 238.

Jean-Jacques Bourguignon et al., "9-Benzyladenines: Potent and Selective cAMP Phosphodiesterase Inhibitors," *J. Med. Chem*, 1997, pp. 1768-1770, vol. 40.

James L. Kelley et al., "6-(Alkyamino)-9-alkylpurines. A New Class of Potential Antipsychotic Agents," *J. Med. Chem.*, 1997, pp. 3207-3216, vol. 40.

Hiroyuki Sawanishi et al., "Selective Inhibitors of Cyclic AMP-Specific Phosphodiesterase: Heterocycle-Condensed Purines", *J. Med. Chem.*, 1997, pp. 3248-3253, vol. 40.

J.E. Sounnes et al., "Proposal for Pharmacologically Distinct Conformers of PDE4 Cyclic AMP Phosphodiesterases", *Ceβ Signal*, 1997, pp. 227-236, vol. 9, No. 3-4.

Mary Elizabeth Bach et al., "Age-related defects in spatial memory are correlated with defects in the late phase of hippocampal long term potentiation in vitro and are attenuated by drugs that enhance the cAMP signaling pathway", *Proc. Natl. Acad. Sci. USA*, Apr. 1999, pp. 5280-5285, vol. 96.

Elisabeth Boichot et al., "Anti-inflammatory Activities of a New Series of Selective Phosphodiesterase 4 Inhibitors Derived from 9-Benzyladenine," *The Journal Of Pharmacology And Experimental Therapeutics*, 2000, pp. 647-653, vol. 292, No. 2.

Japanese Patent Abstract No. 05-001066 dated Jan. 8, 1993.

Japanese Patent Abstract No. 62-240622 dated Oct. 21, 1987.

Japanese Patent Abstract No. 62-010085 dated Jan. 19, 1997.

T. J. Martin, "PDE4 Inhibitors—A Review of the Recent Patent Literature", IDrugs, vol. 4, No. 3, 2001, pp. 312-338.

Japanese Patent Abstract No. 05-001066 dated Jan. 8, 1993.

Japanese Patent Abstract No. 62-240622 dated Oct. 21, 1987.

Japanese Patent Abstract No. 20000-072773, with partial translation.

Raboisson et al., "Design, synthesis and structure—activity relationships of series of 9-substituted adenine derivatives . . . " Eur. J. Med. Chem., 38, 2003, pp. 199-214.

Reimund et al., "Anti-TNF-α Properties of New 9-Benzyladenine Derivatives with Selective . . . ", Biochemical & BioPhysical, (2001), pp. 427-434.

* cited by examiner

PHOSPHODIESTERASE 4 INHIBITORS

This application claims benefit of U.S. Provisional application Ser. No. 60/267,195, filed Feb. 8, 2001, and U.S. Provisional application Ser. No. 60/344,824, filed Jan. 7, 2002.

FIELD OF THE INVENTION

The present invention relates generally to the field of phosphodiesterase 4 (PDE4) enzyme inhibition. More specifically this invention relates to selective PDE4 inhibition by novel adenine analogs, methods of preparing such compounds, compositions containing such compounds, and methods of use thereof.

BACKGROUND OF THE INVENTION

The cyclic nucleotide specific phosphodiesterases (PDEs) represent a family of enzymes that catalyze the hydrolysis of various cyclic nucleoside monophosphates (including cAMP and cGMP). These cyclic nucleotides act as second messengers within cells, and as messengers, carry impulses from cell surface receptors having bound various hormones and neurotransmitters. PDEs act to regulate the level of cyclic nucleotides within cells and maintain cyclic nucleotide homeostasis by degrading such cyclic mononucleotides resulting in termination of their messenger role.

PDE enzymes can be grouped into eleven families according to their specificity toward hydrolysis of cAMP or cGMP, their sensitivity to regulation by calcium, calmodulin or cGMP, and their selective inhibition by various compounds. For example, PDE 1 is stimulated by $Ca^{2+}$/calmodulin. PDE 2 is cGMP-dependent, and is found in the heart and adrenals. PDE 3 is cGMP-dependent, and inhibition of this enzyme creates positive inotropic activity. PDE 4 is cAMP specific, and its inhibition causes airway relaxation, antiinflammatory and antidepressant activity. PDE 5 appears to be important in regulating cGMP content in vascular smooth muscle, and therefore PDE 5 inhibitors may have cardiovascular activity. Since the PDEs possess distinct biochemical properties, it is likely that they are subject to a variety of different forms of regulation.

PDE4 is distinguished by various kinetic properties including low Michaelis constant for cAMP and sensitivity to certain drugs. The PDE4 enzyme family consists of four genes, which produce 4 isoforms of the PDE4 enzyme designated PDE4A, PDE4B, PDE4C, and PDE4D [See: Wang et al., Expression, Purification, and Characterization of human cAMP-Specific Phosphodiesterase (PDE4) Subtypes A, B, C, and D, *Biochem. Biophys. Res. Comm.*, 234, 320-324 (1997)] In addition, various splice variants of each PDE4 isoform have been identified.

PDE4 isoenzymes are localized in the cytosol of cells and are unassociated with any known membranous structures. PDE4 isoenzymes specifically inactivate cAMP by catalyzing its hydrolysis to adenosine 5'-monophosphate (AMP). Regulation of cAMP activity is important in many biological processes, including inflammation and memory. Inhibitors of PDE4 isoenzymes such as rolipram, piclamilast, CDP-840 and ariflo are powerful antiinflammatory agents and therefore may be useful in treating diseases where inflammation is problematic such as asthma or arthritis. Further, rolipram improves the cognitive performance of rats and mice in learning paradigms.

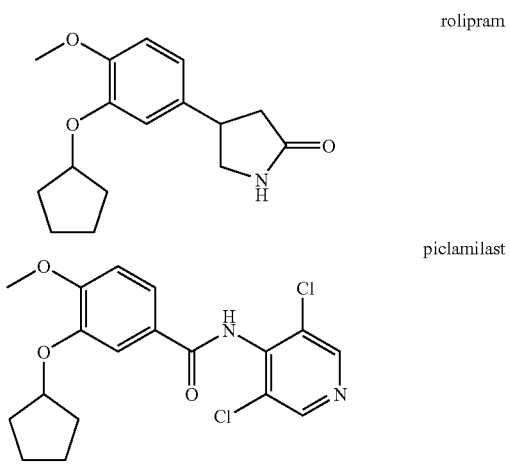

In addition to such compounds as rolipram, xanthine derivatives such as pentoxifylline, denbufylline, and theophylline inhibit PDE4 and have received considerable attention of late for their cognition enhancing effects. cAMP and cGMP are second messengers that mediate cellular responses to many different hormones and neurotransmitters. Thus, therapeutically significant effects may result from PDE inhibition and the resulting increase in intracellular cAMP or cGMP in key cells, such as those located in the nervous system and elsewhere in the body.

Rolipram, previously in development as an anti-depressant, selectively inhibits the PDE4 enzyme and has become a standard agent in the classification of PDE enzyme subtypes. Early work in the PDE4 field focused on depression and inflammation, and has subsequently been extended to include indications such as dementia. [see "The PDE IV Family Of Calcium-Phosphodiesterases Enzymes," John A. Lowe, III, et al., Drugs of the Future 1992, 17(9):799-807 for a general review). Further clinical developments of rolipram and other first-generation PDE4 inhibitors were terminated due to the side effect profile of these compounds. The primary side effect in primates is emesis, while the primary side effects in rodents are testicular degranulation, weakening of vascular smooth muscle, psychotrophic effects, increased gastric acid secretion and stomach erosion.

SUMMARY OF THE INVENTION

The present invention relates to novel adenine compounds that inhibit PDE4 enzymes, and especially have improved side effect profiles, e.g., are relatively non-emetic, (e.g., as compared to the previously discussed prior art compounds). In particular, the present invention relates to novel 9-substituted-2-trifluoromethyladenine compounds that possess PDE4 inhibitory activity. Preferably, the compounds selectively inhibit PDE4 enzymes. The compounds of this invention at the same time facilitate entry into cells, especially cells of the nervous system.

Still further, the present invention provides methods for synthesizing compounds with such activity and selectivity as well as methods of (and corresponding pharmaceutical compositions for) treating a patient, e.g., mammals, including humans, requiring PDE inhibition, especially PDE4 inhibition, for a disease state that involves elevated intracellular PDE 4 levels or decreased cAMP levels, e.g., involving neurological syndromes, especially those states associated with memory impairment, most especially long term memory impairment, as where such memory impairment is due in part to catabolism of intracellular cAMP levels by PDE 4 enzymes, or where such memory impairment may be improved by effectively inhibiting PDE4 enzyme activity.

In a preferred aspect, the compounds of the invention improve such diseases by inhibiting PDE4 enzymes at doses which do not induce emesis.

Upon further study of the specification and appended claims, further aspects, objects and advantages of this invention will become apparent to those skilled in the art.

The present invention includes compounds of Formula I:

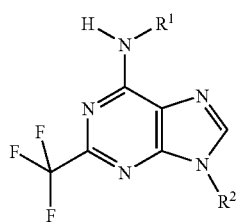

wherein, $R^1$ is H, alkyl having 1 to 5 carbon atoms, which is unsustituted or substituted one or more times by halogen, hydroxy, or combinations thereof, and wherein a —CH$_2$— group can be optionally replaced by —O—, —S—, or —NH—, cycloalkyl having 3 to 6 carbon atoms, or cycloalkylalkyl having 4 to 7 C atoms;

$R^2$ is alkyl having 1 to 12 carbon atoms, which is unsubstituted or substituted one or more times by halogen, hydroxy, cyano or combinations thereof, wherein one or more —CH$_2$— groups is each independently optionally replaced by —O—, —S—, or —NH—, and wherein optionally one or more —CH$_2$CH$_2$— groups is replaced in each case by —CH=CH— or —C≡C—, alkyl ether having 3 to 12 carbon atoms, cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times in by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylmedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof, with the provisos that:

(a) when $R^1$ is methyl, then $R^2$ is not arylalkyl, heteroarylalkyl, 2-(1,2,3,4-tetrahydro)quinolinyl-methyl, methyl or 2-butyl;

(b) when $R^1$ is cyclopropyl, $R^2$ is not 4-methylbenzyl;

(c) when $R^1$ is ethyl, then $R^2$ is not ethyl, 3-aminobenzyl, 2-thienylmethyl, 3-thienylmethyl, or 2-pyridylmethyl;

(d) when $R^1$ is cyclopropyl, then $R^2$ is not cyclopropylmethyl;

(e) when $R^1$ is H, then $R^2$ is not methyl, ethyl, benzyl, 4-methylbenzyl, or substituted tetrahydrofuranyl;

(f) when $R^1$ is methoxyethyl, then $R^2$ is not benzyl, 3-dimethylaminobenzyl, or 3-thienylmethyl;

(g) when $R^1$ is iso-butyl, then $R^2$ is not benzyl; and (h) when $R^1$ is n-butyl, then $R^2$ is not n-butyl.

According to a further aspect of the invention there is provided a genus according to formula I wherein when $R^1$ is methyl, $R^2$ is not arylalkyl, heteroarylalkyl, 2-(1,2,3,4-tetrahydro)quinolinyl-methyl or $C_{1-5}$-alkyl.

According to a further aspect of the invention there is provided a genus according to formula I wherein when $R^1$ is methyl, $R^2$ is not arylalkyl, heteroarylalkyl, heterocyclealkyl or $C_{1-5}$-alkyl.

According to a further aspect of the invention there is provided a genus according to formula I wherein when $R^1$ is cyclopropyl, $R^2$ is not arylalkyl.

According to a further aspect of the invention there is provided a genus according to formula I wherein when $R^1$ is ethyl, $R^2$ is not arylalkyl, heteroarylalkyl, or $C_{1-3}$-alkyl.

According to a further aspect of the invention there is provided a genus according to formula I wherein when $R^1$ is cyclopropyl, $R^2$ is not cycloalkylalkyl.

According to a further aspect of the invention there is provided a genus according to formula I wherein when $R^1$ is H, $R^2$ is not arylalkyl, heterocycle or $C_{1-3}$-alkyl.

According to a further aspect of the invention there is provided a genus according to formula I wherein when $R^1$ is methoxyethyl, $R^2$ is not arylalkyl or heteroarylalkyl.

According to a further aspect of the invention there is provided a genus according to formula I wherein when $R^1$ is a butyl group, $R^2$ is not arylalkyl or $C_{1-5}$-alkyl.

According to a preferred aspect of the invention there is provided a genus of novel compounds according to formula II wherein
$R^{1'}$ is methyl, ethyl, or cyclopropyl; and
$R^{2'}$ is cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof,
heterocycle having 5 to 10 ring atoms in which at least 1 ring atom is a heteroatom, which is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), or
carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof.

According to a further aspect of the invention there is provided a genus of novel compounds according to the Formula III:

wherein
$R^{1''}$ is H,
alkyl having 1 to 5 carbon atoms,
alkyl having 1 to 5 carbon atoms which is substituted one or more times by halogen, hydroxy, oxo, cyano or combinations thereof,
cycloalkyl having 3 to 6 carbon atoms,
cycloalkyl having 3 to 6 carbon atoms, which is substituted one or more times by halogen, alkyl, oxo or combinations thereof,
cycloalkylalkyl having 4 to 7 C atoms,
cycloalkylalkyl having 4 to 7 C atoms, which is substituted one or more times by $C_{1-4}$ alkyl, halogen, halogenated $C_{1-4}$ alkyl, or combinations thereof,
$R^{2''}$ is alkyl having 1 to 12 carbon atoms,
alkyl having 1 to 12 carbon atoms which is substituted one or more times by halogen, hydroxy, oxo, cyano or combinations thereof,
alkyl ether having 3 to 12 carbon atoms,
cycloalkyl having 3 to 12 carbon atoms,
cycloalkyl having 3 to 12 carbon atoms which is substituted one or more times by halogen, $C_{1-4}$ alkyl, oxo or combinations thereof,
cycloalkylalkyl having 4 to 12 C atoms, cycloalkylalkyl having 4 to 12 C atoms, which is substituted one or more times by C$_{1-4}$ alkyl, halogen, halogenated C$_{1-4}$ alkyl, or combinations thereof, aryl having 6 to 10 carbon atoms, aryl having 6 to 10 carbon atoms which is substituted one or more times by halogen, C$_{1-4}$ alkyl, halogenated C$_{1-4}$ alkyl, hydroxy, C$_{1-4}$-alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, C$_{2-4}$, acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof, arylalkyl having 7 to 16 carbon atoms, arylalkyl having 7 to 16 carbon atoms which is substituted one or more times by halogen, C$_{1-4}$ alkyl, halogenated C$_{1-4}$ alkyl, hydroxy, C$_{1-4}$-alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, C$_{2-4}$, acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof, heteroaryl having 5 to 10 ring atoms in which at least 1 ring atom is a heteroatom, substituted heteroaryl having 5 to 10 ring atoms, in which at least 1 ring atom is a heteroatom, which is substituted one or more times by halogen, aryl, C$_{1-4}$-alkyl, C$_{1-4}$-alkoxy, cyano, trifluoromethyl, nitro, oxo, amino, C$_{1-4}$-alkylamino, di-C$_{1-4}$-alkylamino or combinations thereof, heteroarylalkyl having 5 to 10 ring atoms in which at least 1 ring atom is a heteroatom, or substituted heteroarylalkyl having 5 to 10 ring atoms in which at least 1 ring atom is a heteroatom and which is substituted one or more times in the heteroaryl portion by halogen, aryl, C$_{1-4}$-alkyl, C$_{1-4}$-alkoxy, cyano, trifluoromethyl, nitro, oxo, amino, C$_{1-4}$-alkylamino, di-C$_{1-4}$-alkylamino or combinations thereof and/or substituted in the alkyl portion by halogen, oxo, cyano, or combinations thereof;

and pharmaceutically acceptable salts thereof, with the provisos that (a) when R$^{1''}$ is methyl, then R$^{2''}$ is not arylalkyl, heteroarylalkyl, methyl or 2-butyl, (b) when R$^{1''}$ is cyclopropyl, R$^{2''}$ is not 4-methylbenzyl, (c) when R$^{1''}$ is ethyl, then R$^{2''}$ is not ethyl, and (d) when R$^{1''}$ is cyclopropyl, then R$^{2''}$ is not cyclopropylmethyl.

In accordance with a further aspect of the invention, there is provided a genus of formula III in which R$^{1''}$ and R$^{2''}$ are in accordance with the following subformulas:

IIIa R$^{1''}$ is cyclopropyl; and
R$^{2''}$ is cycloalkyl.

IIIb R$^{1''}$ is methyl; and
R$^{2''}$ is cycloalkyl.

IIIc R$^{1''}$ is methyl, ethyl, cyclopropyl; and
R$^{2''}$ is phenyl or substituted phenyl.

IIId R$^{1''}$ is methyl, ethyl, cyclopropyl; and
R$^{2''}$ is heteroaryl or substituted heteroaryl.

The compounds of the present invention are effective in inhibiting, or modulating the activity of PDE4 in animals, e.g., mammals, especially humans. These compounds exhibit neurological activity, especially where such activity affects cognition, including long term memory. These compounds will also be effective in treating diseases where decreased cAMP levels are involved. This includes but is not limited to inflammatory diseases. These compounds may also function as antidepressants, or be useful in treating cognitive and negative symptoms of schizophrenia.

In accordance with the method aspect of the invention, there is provided a method of treating a patient (e.g., a mammal such as a human) suffering from a disease state (e.g., memory impairment, inflammatory disesases, depression, etc.) involving decreased cAMP levels and/or increased intracellular PDE4 levels, comprising administering to the patient a compound according to formula I$^a$:

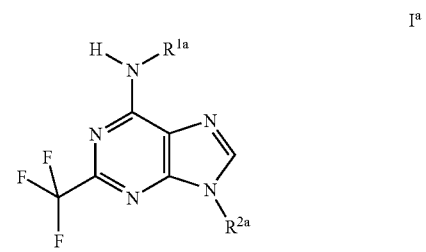

wherein,

R$^{1a}$ is H,
alkyl having 1 to 5 carbon atoms, which is unsustituted or substituted one or more times by halogen, hydroxy, or combinations thereof, and wherein a —CH$_2$— group can be optionally replaced by —O—, —S—, or —NH—, cycloalkyl having 3 to 6 carbon atoms, or cycloalkylalkyl having 4 to 7 C atoms;

R$^{2a}$ is alkyl having 1 to 12 carbon atoms, which is unsubstituted or substituted one or more times by halogen, hydroxy, cyano or combinations thereof, wherein one or more —CH$_2$— groups is each independently optionally replaced by —O—, —S—, or —NH—, and wherein optionally one or more —CH$_2$CH$_2$— groups is replaced in each case by —CH=CH— or —C≡C— alkyl ether having 3 to 12 carbon atoms, cycloalkyl having 3 to 12 carbon atoms, which is unsubstituted or substituted one or more times by halogen, C$_{1-4}$ alkyl, halogenated C$_{1-4}$ alkyl, C$_{1-4}$ alkoxy, cyano or combinations thereof, cycloalkylalkyl having 4 to 12 C atoms, which is unsubstituted or substituted one or more times by C$_{1-4}$ alkyl, halogenated C$_{1-4}$ alkyl, C$_{1-4}$ alkoxy, cyano, halogen, or combinations thereof, aryl having 6 to 14 carbon atoms, which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, hydroxamic acid, carboxamide, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof, arylalkyl having 7 to 16 carbon atoms, which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, hydroxamic acid, carboxamide, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times in by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof, with the provisos that:

(a) when $R^{1a}$ is methyl, then $R^{2a}$ is not arylalkyl, heteroarylalkyl, 2-(1,2,3,4-tetrahydro)quinolinyl-methyl, methyl or 2-butyl;

(b) when $R^{1a}$ is cyclopropyl, $R^{2a}$ is not 4-methylbenzyl;

(c) when $R^{1a}$ is ethyl, then $R^{2a}$ is not ethyl, 3-aminobenzyl, 2-thienylmethyl, 3-thienylmethyl, or 2-pyridylmethyl;

(d) when $R^{1a}$ is cyclopropyl, then $R^{2a}$ is not cyclopropylmethyl;

(e) when $R^{1a}$ is H, then $R^{2a}$ is not methyl, ethyl, benzyl, 4-methylbenzyl, or substituted tetrahydrofuranyl;

(f) when $R^{1a}$ is methoxyethyl, then $R^{2a}$ is not benzyl, 3-dimethylaminobenzyl, or 3-thienyhnethyl;

(g) when $R^{1a}$ is iso-butyl, then $R^{2a}$ is not benzyl; and (h) when $R^{1a}$ is n-butyl, then $R^{2a}$ is not n-butyl.

In accordance with the method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound according to formula $I^b$:

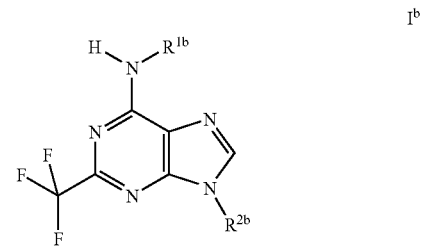

wherein, $R^{1b}$ is H, alkyl having 1 to 5 carbon atoms, which is unsustituted or substituted one or more times by halogen, hydroxy, or combinations thereof, and wherein a —$CH_2$— group can be optionally replaced by —O—, —S—, or —NH—, cycloalkyl having 3 to 6 carbon atoms, or cycloalkylalkyl having 4 to 7 C atoms;

$R^{2b}$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C— alkyl ether having 3 to 12 carbon atoms, cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$- acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsustituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times in by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof, with the provisos that when $R^{1b}$ is methyl, then $R^{2b}$ is not arylalkyl, methyl or 2-butyl, and when $R^{1b}$ is H, then $R^{2b}$ is not benzyl.

In accordance with a further method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound according to formula $I^c$:

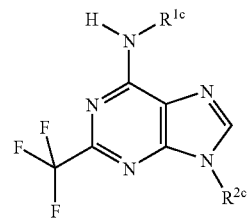

wherein, $R^{1c}$ is H, alkyl having 1 to 5 carbon atoms, which is unsustituted or substituted one or more times by halogen, hydroxy, or combinations thereof, and wherein a —$CH_2$— group can be optionally replaced by —O—, —S—, or —NH—, cycloalkyl having 3 to 6 carbon atoms, or cycloalkylalkyl having 4 to 7 C atoms;

$R^{2c}$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH═CH— or —C≡C— alkyl ether having 3 to 12 carbon atoms, cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 12 C atoms, which is unsubstituted or substituted one or more times by $C_{1-4}$ alkyl, halogenated $C_{1-4}$ alkyl, $C_{1-4}$ alkoxy, cyano, halogen, or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times in by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), heterocycle-alkyl wherein the heterocycle portion has 5 to 10 ring atoms in which at least 1 ring atom is a heteroatom and the alkyl portion has 1 to 3 carbon atoms, the heterocycle portion is nonarmoatic and is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl-ethyl and pyrrolinyl-methyl), or carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof, with the proviso that said compound is not 6-methylamino-9-(2-fluorobenzyl)-2-trifluoromethylpurine.

In accordance with a further method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound according to formula II

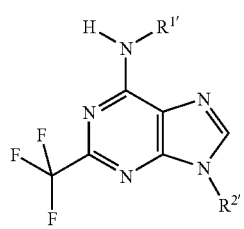

II wherein $R^{1'}$ is methyl, ethyl, or cyclopropyl; and $R^{2'}$ is cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, hydroxamic acid, carboxamide, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times in the by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof (e.g., piperidinyl, imidazolinyl, imidazolidinyl, pyrrolinyl, pyrrolidinyl, morpholinyl, piperazinyl, and indolinyl), or carbocycle which is nonaromatic, monocyclic or bicyclic, group having 5 to 14 carbon atoms, which is unsubstituted or is substituted one or more times in the by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, hydroxamic acid, carboxamide, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof;

and pharmaceutically acceptable salts thereof.

In accordance with a further method aspect of the invention, there is provided a method of treating a patient (e.g., a mammal such as a human) suffering from a disease state (e.g., memory impairment) involving decreased cAMP levels and/or increased intracellular PDE4 levels, comprising administering to the patient a compound according to formula III$^a$:

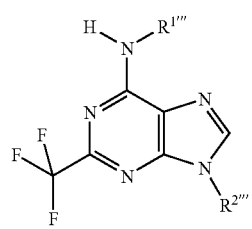

III$^a$ wherein,

R$^{1'''}$ is H,
alkyl having 1 to 5 carbon atoms, which is unsustituted or is substituted one or more times by halogen, hydroxy, oxo, cyano or combinations thereof,
cycloalkyl having 3 to 6 carbon atoms, which is unsubstituted or is substituted one or more times by halogen, alkyl, oxo or combinations thereof, or
cycloalkylalkyl having 4 to 7 C atoms, which is unsubstituted or is substituted one or more times by C$_{1-4}$ alkyl, halogen, halogenated C$_{1-4}$ alkyl, or combinations thereof; and R$^{2'''}$ is alkyl having 1 to 12 carbon atoms, which is unsustituted or which is substituted one or more times by halogen, hydroxy, oxo, cyano or combinations thereof, alkyl ether having 3 to 12 carbon atoms,
cycloalkyl having 3 to 12 carbon atoms, which is unsubstituted or which is substituted one or more times by halogen, C$_{1-4}$ alkyl, oxo or combinations thereof,
cycloalkylalkyl having 4 to 12 C atoms, which is unsubstituted or is substituted one or more times by C$_{1-4}$ alkyl, halogen, halogenated C$_{1-4}$ alkyl, or combinations thereof,
aryl having 6 to 10 carbon atoms, which is unsubstituted or is substituted one or more times by halogen, C$_{1-4}$ alkyl, halogenated C$_{1-4}$ alkyl, hydroxy, C$_{1-4}$-alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof,
arylalkyl having 7 to 16 carbon atoms, which is unsubstituted or is substituted one or more times by halogen, C$_{1-4}$ alkyl, halogenated C$_{1-4}$ alkyl, hydroxy, C$_{1-4}$-alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof,
heteroaryl having 5 to 10 ring atoms in which at least 1 ring atom is a heteroatom, substituted heteroaryl having 5 to 10 ring atoms, in which at least 1 ring atom is a heteroatom, which is substituted one or more times by halogen, aryl, C$_{1-4}$-alkyl, C$_{1-4}$-alkoxy, cyano, trifluoromethyl, nitro, oxo, amino, C$_{1-4}$-alkylamino, di-C$_{1-4}$-alkylamino or combinations thereof, or
heteroarylalkyl having 5 to 10 ring atoms in which at least 1 ring atom is a heteroatom, which is unsubstituted or is substituted one or more times in the heteroaryl portion by halogen, aryl, C$_{1-4}$-alkyl, C$_{1-4}$-alkoxy, cyano, trifluoromethyl, nitro, oxo, amino, C$_{1-4}$-alkylamino, di-C$_{1-4}$-alkylamino or combinations thereof and/or substituted in the alkyl portion by halogen, oxo, cyano, or combinations thereof; and
pharmaceutically acceptable salts thereof,
with the proviso that
(a) when R$^{1'''}$ is methyl, then R$^{2'''}$ is not arylalkyl, heteroarylalkyl, methyl or 2-butyl.

In formula III$^a$, R$^{1'''}$ is preferably methyl, ethyl or cyclopropyl.

Assays for determining PDE inhibiting activity as well as selectivity of PDE 4 inhibiting activity and selectivity of inhibiting PDE 4 isoenzymes are known within the art. See, e.g., U.S. Pat. No. 6,136,821, the disclosure of which is incorporated herein by reference.

Halogen herein refers to F, Cl, Br, and I. Preferred halogens are F and Cl.

Alkyl, as a group or substituent per se or as part of a group or substituent (e.g., alkylamino, trialkylsilyloxy, aminoalkyl, hydroxyalkyl), means a straight-chain or branched-chain aliphatic hydrocarbon radical having 1 to 12 carbon atoms, preferably 1 to 8 carbon atoms, especially 1 to 4 carbon atoms.

Alkyl radicals for R$^1$ have up to 5 carbon atoms, preferably 1 to 4 carbon atoms, especially 1 to 3 carbon atoms. Suitable alkyl groups for R$^1$ include methyl, ethyl, propyl, isopropyl, butyl, isopropyl and pentyl. Other examples of suitable alkyl groups for R$^1$ include 1-, 2- or 3-methylbutyl, 1,1-, 1,2- or 2,2-dimethylpropyl and 1-ethylpropyl.

Alkyl radicals for R$^2$ have up to 12 carbon atoms, preferably 3 to 8 carbon atoms, especially 3 to 6 carbon atoms. Suitable alkyl groups for R$^2$ include those listed above for R$^1$ as well as hexyl, heptyl, octyl, nonyl, decyl, undecyl, dodecyl, 1-, 2-, 3- or 4-methylpentyl, tert-butyl, 1,1-, 1,2-, 1,3-, 2,2-, 2,3- or 3,3-dimethylbutyl, 1- or 2-ethylbutyl, ethylnethylpropyl, trimethylpropyl, methylhexyl, dimethylpentyl, ethylpentyl, ethylmethylbutyl, dimethylbutyl, and the like.

Substituted alkyl groups are alkyl groups as described above which are substituted in one or more positions by, for example, halogens, oxo, hydroxy, C$_{1-4}$-alkoxy, halogenated C$_{1-4}$-alkoxy, and/or cyano. Halogens are preferred substituents, especially F and Cl.

Alkoxy groups means alkyl-O— groups in which the alkyl portion is in accordance with the previous discussion. Suitable alkoxy groups are methoxy, ethoxy, propoxy and butoxy, pentoxy, hexoxy, heptoxy, octoxy and trifluoromethoxy. Preferred alkoxy groups are methoxy and ethoxy. Similarly, alkoxycarbonyl means alkyl —O—CO— in which the alkyl portion is in accordance with the previous discussion. Examples include methoxycarbonyl, ethoxycarbonyl, propoxycarbonyl, and tert-butoxycarbonyl.

Alkenyl refers to straight-chain or branched-chain aliphatic radicals containing 2 to 12 carbon atoms in which one or more —CH$_2$—CH$_2$— structures are each replaced by —CH═CH—. Suitable alkenyl groups are ethenyl, 1-propenyl, 2-methylethenyl, 1-butene, 2-butene, 1-pentenyl, and 2-pentenyl.

Alkynyl refers to straight-chain or branched-chain aliphatic radicals containing 2 to 12 carbon atoms in which one or more —CH$_2$—CH$_2$— structures are each replaced by —C≡C—. Suitable alkynyl groups are ethynyl, propynyl, 1-butynyl, and 2-butynyl.

Cycloalkyl means a monocyclic, bicyclic or tricyclic nonaromatic saturated hydrocarbon radical. Cycloalkyl radicals for R$^1$ have 3 to 6 carbon atoms, preferably 3 to 5 carbon atoms, especially 3 carbon atoms. Suitable cycloalkyl groups for R$^1$ include cyclopropyl, cyclobutyl, cyclopentyl and cyclohexyl. Cycloalkyl radicals for R$^2$ have 3 to 12 carbon atoms, preferably 3 to 10 carbon atoms, especially 4 to 8 carbon atoms. Suitable cycloalkyl groups for R$^2$ include those listed above for R$^1$ as well as cycloheptyl, cyclooctyl, cyclononyl, norbornyl, 1-decalin, adamant-1-yl, and adamant-2-yl. Other suitable cycloalkyl groups for R$^2$ include spiro[2,4]heptyl, spiro[2.5]octyl, bicyclo[5.1.0]octyl, bicyclo[2.2.0]hexyl, spiro[3.3]heptyl, and bicyclo[4.2.0]octyl.

The cycloalkyl group can be substituted. For example, it can be substituted by halogens, C$_{1-4}$-alkyls, C$_{1-4}$-halogenated alkyls, C$_{1-4}$-alkoxy and/or cyano.

Cycloalkylalkyl refers to cycloalkyl-alkyl radicals in which the cycloalkyl and alkyl portions are in accordance with previous discussions. Suitable examples include cyclopropylmethyl and cyclopentylmethyl.

Alkyl ethers refer to $C_3$ to $C_{12}$ alkoxyalkyl radicals. Suitable alkyl ether groups include methoxyethyl, ethoxyethyl, and methoxypropyl.

Aryl, as a group or substituent per se or as part of a group or substituent, refers to an aromatic carbocyclic radical containing 6 to 14 carbon atoms, preferably 6 to 12 carbon atoms, especially 6 to 10 carbon atoms. Suitable aryl groups include phenyl, naphthyl and biphenyl. Substituted aryl groups include the above-described aryl groups which are substituted one or more times by, for example, by halogen, $C_{1-4}$-alkyl, $C_{1-4}$-halogenated alkyl, hydroxy, $C_{1-4}$-alkoxy, $C_{1-4}$-halogenated alkoxy, nitro, methylenedioxy, ethylenedioxy, amino, $C_{1-4}$-alkylamino, di-$C_{1-4}$-alkylamino, $C_{1-4}$-hydroxyalkyl, $C_{1-4}$-hydroxyalkoxy, carboxy, cyano, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl and phenoxy.

Arylalkyl refers to an aryl-alkyl-radical in which the aryl and alkyl portions are in accordance with the previous descriptions. Preferably, the aryl portion has 6 to 10 carbon atoms and the alkyl portion, which is straight-chained or branched, has 1 to 6 carbon atoms, preferably 1 to 3 carbon atoms. The aryl portion can be substituted by the substituents described above for aryl groups and the alkyl portion can be substituted by oxo, halogens, cyano or combinations thereof. Suitable examples include benzyl, 1-phenethyl, 2-phenethyl, phenpropyl, fluorobenzyl, chlorobenzyl, methoxybenzyl, methylbenzyl and cyanobenzyl.

Heteroaryl refers to an aromatic heterocyclic group having one or two rings and a total number of 5 to 10 ring atoms wherein at least one of the ring atoms is a heteroatom. Preferably, the heteroaryl group contains 1 to 3, especially 1 or 2, hetero-ring atoms which are selected from N, O and S. Suitable heteroaryl groups include furyl, thienyl, pyrrolyl, pyrazolyl, imidazolyl, triazolyl, tetrazolyl, isoxazolyl, oxazolyl, thiazolyl, isothiazolyl, oxadiazolyl, oxatriazolyl, thiadiazolyl, pyridyl, pyridazinyl, pyrimidinyl, benzofuranyl, isobenzofuranyl, thionaphthenyl, isothionaphthenyl, indolyl, isoindolyl, indazolyl, benzisoxazolyl, benzoxazolyl, benzthiazolyl, benzisothiazolyl, purinyl, benzopyranyl, quinolinyl, isoquinolinyl, cinnolinyl, quinazolinyl, naphthyridinyl, and benzoxazinyl, e.g., 2-thienyl, 3-thienyl, 2-, 3- or 4-pyridyl, 2-, 3-, 4-, 5-, 6-, 7- or 8-quinolinyl, and 1-, 3-, 4-, 5-, 6-, 7- or 8-isoquinolinyl.

Substituted heteroaryl refers to the heteroaryl groups described above which are substituted in one or more places by, for example, halogen, hydroxyl, aryl, alkyl, alkoxy, carboxy, methylene, cyano, trifluoromethyl, nitro, oxo, amino, alkylamino, and dialkylamino.

Heteroarylalkyl refers to a heteroaryl-alkyl-group wherein the heteroaryl and alkyl portions are in accordance with the previous discussions. Suitable examples are pyridylmethyl, thienylmethyl, pyrimidinylmethyl, pyrazinylmethyl, and isoquinolinylmethyl.

Heterocycles are non-aromatic cyclic groups containing at least one hetero-ring atom, preferably selected from N, S and O, for example, 3-tetrahydrofuranyl, piperidinyl, imidazolinyl, imidazolidinyl, pyrrolinyl, pyrrolidinyl, morpholinyl, piperazinyl, and indolinyl.

Heterocycle-alkyl refers to a heterocycle-alkyl-group wherein the heterocyclic and alkyl portions are in accordance with the previous discussions. Suitable examples are piperidinyl-ethyl and pyrrolinyl-methyl.

Carbocycles are non-aromatic monocyclic or bicyclic structures containing 5 to 14 carbon atoms, preferably 6 to 10 carbon atoms. Suitable examples are cyclopentenyl, cyclohexenyl, cyclohexadienyl, tetrahydronaphthenyl and indan-2-yl.

Acyl refers to alkanoyl radicals having 1 to 6 carbon atoms in which the alkyl portion can be substituted by halogen, alkyl, aryl and/or alkoxy, or aroyl radicals having 7 to 15 carbon atoms in which the aryl portion can be substituted by, for example, halogen, alkyl and/or alkoxy. Suitable acyl groups include formyl, acetyl, propionyl, butanoyl and benzoyl.

Substituted radicals preferably have 1 to 3 substituents, especially 1 to 2 substituents.

$R^1$ is preferably H, alkyl such as methyl, ethyl and isopropyl, substituted alkyl, such as HOCH$_2$CH$_2$—, cycloalkyl such as cyclopropyl, cyclobutyl, and cyclopentyl, cycloalkylalkyl such as cyclopropylmethyl. In particular, $R^1$ is preferably methyl, ethyl or cycloalkyl such as cyclopropyl, cyclobutyl, or cyclopentyl, especially methyl, ethyl and cyclopropyl.

$R^2$ is preferably cycloalkyl, aryl, heteroaryl, carbocycle or hetero cycle. In particular, $R^2$ is preferably cycloalkyl such as cyclopentyl, cyclohexyl, cycloheptyl and norbornyl, aryl which is unsubstituted or substituted one or more times by, e.g., halogen, methoxy, nitro, cyano, amino or combinations thereof, heteroaryl such as pyridinyl, pyrimidinyl, thienyl, and furanyl which is unsubstituted or substituted by, for example, methoxy and/or methylthio, carbocycle such as substituted or unsubstituted 2-indanyl, or heterocycle such as substituted or unsubstituted piperidinyl, pyrrolydinyl, and tetrahydrofuranyl.

In addition, preferred PDE4 inhibitors, in accordance with the invention, are compounds described by subformulas Ia-II, which correspond to formula I, but exhibit the following preferred groups:

Ia $R^1$ is alkyl having 1 to 5 C atoms which is unsubstituted or substituted by hydroxy, cycloalkylalkyl having 4 to 6 carbon atoms, or is cycloalkyl having 3-5 C atoms; and $R^2$ is alkyl having 3 to 8 C atoms, alkyl ether having 3 to 8 carbon atoms, cycloalkyl having 3 to 9 carbon atoms, cycloalkylalkyl having 4 to 10 carbon atoms, aryl having 6 to 10 carbon atoms, heterocycle having 5 to 10 ring atoms, heterocycle having 5 to 10 ring atoms, heterocycle-alkyl having 5 to 10 ring atoms, carbocycle having 5 to 12 carbon atoms, or heteroaryl, heteroarylalkyl or arylalkyl having 7 to 12 C atoms, wherein the heteroaryl or aryl portion is unsubstituted or substituted one more times by halogens, alkyl, CN, alkoxy, nitro, alkoxy, or the combinations thereof and the alkyl portion is unsubstituted or substituted by halogen thereof.

Ib $R^1$ is cyclopropyl; and $R^2$ is benzyl, phenethyl, or phenpropyl, which in each case is substituted 1 to 3 times by halogens, $C_{1-4}$ alkyl, $C_{1-4}$ alkoxy or combinations thereof.

Ic $R^1$ is cyclopropyl; and $R^2$ is alkyl having 3 to 8 C atoms or arylalkyl having 7 to 12 C atoms wherein the aryl portion is substituted one more time by halogens, alkyl, CN, alkoxy, nitro, or combinations thereof.

Id R$^1$ is cyclopropyl; and
R$^2$ is benzyl, 2-methylbenzyl, 3-methylbenzyl, 2-chlorobenzyl, 3-chlorobenzyl, 4-chlorobenzyl, 2-fluorobenzyl, 3-fluorobenzyl, 4-fluorobenzyl, 3-methoxybenzyl, 4-cyanobenzyl, 2-triflouromethylbenzyl, 3-trifluoromethylbenzyl, 4-trifluoromethylbenzyl, 3,5-di(trifluoromethyl)benzyl, 2,4-difluorobenzyl, 3,4-difluorobenzyl, 3,5-difluorobenzyl, 2,6-difluorobenzyl, 2,3-difluorobenzyl, 2-chloro-4-fluorobenzyl, 3-chloro-4-chlorobenzyl, 2-chloro-phenethyl, 2-fluoro-phenethyl, 2-methyl-phenethyl, 3-chlorophenethyl, 3-methylphenethyl, 3-methylphenethyl, 3-methoxyphenethyl, 4-chlorophenethyl, 4-methylphenethyl, 4-methoxyphenethyl, 2-methoxy-phenpropyl, 4-chloro-phenpropyl, 4-methoxyphenpropyl.

Ie R$^1$ is cyclopropyl; and
R$^2$ is heteroarylalkyl which is unsubstituted or substituted 1 to 3 halogen, C$_{1-4}$-alkyl, C$_{1-4}$-alkoxy or combinations thereof.

If R$^1$ is cyclopropyl; and
R$^2$ is 2-pyridylmethyl, 3-pyridylmethyl, 4-pyridylmethyl, 2-thienylmethyl, 3-thienylmethyl, 2-furylmethyl or 3-furylmethyl.

Ig R$^1$ is methyl, ethyl, or cyclopropyl; and
R$^2$ is cycloalkyl.

Ih R$^1$ is methyl, ethyl, or cyclopropyl; and
R$^2$ is cyclobutyl, cyclopentyl, cyclohexyl, cycloheptyl or norbornyl.

Ii R$^1$ is methyl, ethyl, or cyclopropyl; and
R$^2$ is aryl (e.g., phenyl) or substituted aryl (e.g., substituted phenyl).

Ij R$^1$ is methyl, ethyl, or cyclopropyl; and
R$^2$ is carbocycle (e.g., 2-indanyl).

Ik R$^1$ is methyl, ethyl, or cyclopropyl; and
R$^2$ is heterocycle (e.g., piperidinyl).

Il R$^1$ is methyl, ethyl, or cyclopropyl; and
R$^2$ is heteroaryl or substituted heteroaryl (e.g., substituted or unsubstituted pyrimdinyl, pyridyl, thienyl, and furanyl.

Preferred aspects include pharmaceutical compositions comprising a compound of this invention and a pharmaceutically acceptable carrier and, optionally, another active agent as discussed below; a method of inhibiting a PDE4 enzyme, especially an isoenzyme, e.g., as determined by a conventional assay or one described herein, either in vitro or in vivo (in an animal, e.g., in an animal model, or in a mammal or in a human); a method of treating neurological syndrome, e.g., loss of memory, especially long-term memory, cognitive impairment or decline, memory impairment, etc.; a method of treating a disease state modulated by PDE4 activity, in a mammal, e.g., a human, e.g., those mentioned herein.

The compounds of the present invention may be prepared conventionally. Some of the processes which can be used are described below. All starting materials are known or can be conventionally prepared from known starting materials.

2-Substituted hypoxanthines are produced by standard methods in the art, such as by neat reaction between 4-amino-5-imidazolecarboxamide and 2,2,2-trifluoroacetamide (E. Richter et al, J. Am. Chem. Soc. 1960, 82, 3144-3146; or A. Giner-Sorala, et al, J. Am. Chem. Soc. 1958, 80, 5744-5752; or A. Parkin, et al, J. Heterocycl. Chem. 1982, 19, 33-40). 6-Halo-2-trifluoromethylpurine may be prepared by methods common in the art (see J.-J. Bourguignon, et al., J. Med. Chem. 1997, 40, 1768-1770; and H. Bader, et al., U.S. Pat. No. 4,405,781, 1983) such as by reaction with a halogenating reagent such as with SOCl$_2$, or POCl$_3$, or PCl$_5$. These reactions can be run neat or with a polar aprotic solvent such as dichloromethane, dichloroethane, or N,N-dimethylformamide. Reaction of a 6-halopurine (e.g. 6-chloro-2-trifluoromethylpurine) with either an alkyl halide, cycloalkyl halide, cycloalkylalkyl halide, heteroaryl halide or arylalkyl halide in a polar aprotic solvent such as N,N-dimethylforamide, dimethylsulfoxide, or dimethoxyethane in the presence of a base (e.g. K$_2$CO$_3$, Na$_2$CO$_3$, NaH) provides a mixture of 9- and 7-substituted 6-halopurines.

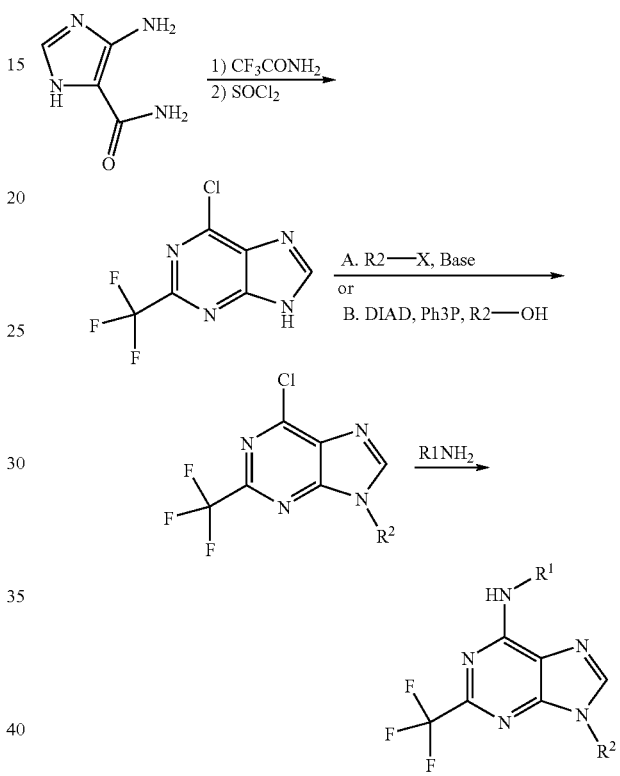

The use of a phase transfer catalyst, for example, 18-crown-6 or tetrabutylammonium chloride, with increased reaction temperature, e.g., 60° C. to 150° C., can be used to enhance reaction rates or reaction yields. Alternatively, reaction of a 6-halopurine under Mitsunobu conditions with an alkyl alcohol, cycloalkyl alcohol, arylalkyl alcohol, heteroaryl alcohol, or cycloalkylalkyl alcohol provides a mixture of 9- and 7-substituted 6-halopurines. The 9- and 7-isomers produced by the reactions described above are readily separated by chromatography. Such 9-substituted-6-halopurines undergo reaction with amines (e.g. anmmonia, alkylamines, cycloalkylamines, or cycloalkylalkylamines) to provide adenine derivatives of formulas I-III.

Alternatively, 6-halo-2-substituted purines readily undergo reaction with amines (e.g. ammonia, alkylamines, cycloalkylamines, or cycloalkylalkylamines) in the presence of polar protic solvents (e.g. methanol, ethanol, propanol etc.) to yield 6-N-substituted adenine analogs. Reaction with either an alkyl halide, cycloalkyl halide, cycloalkylalkyl halide, heteroaryl halide or arylalkyl halide in a polar aprotic solvent such as N,N-dimethylformamide, dimethylsulfoxide, or dimethoxyethane, and in the presence of a base (e.g. K$_2$CO$_3$, Na$_2$CO$_3$, NaH) provides adenine derivatives of formulas I-III. The use of a phase transfer catalyst, for example, 18-crown-6 or tetrabutylammonium chloride, with

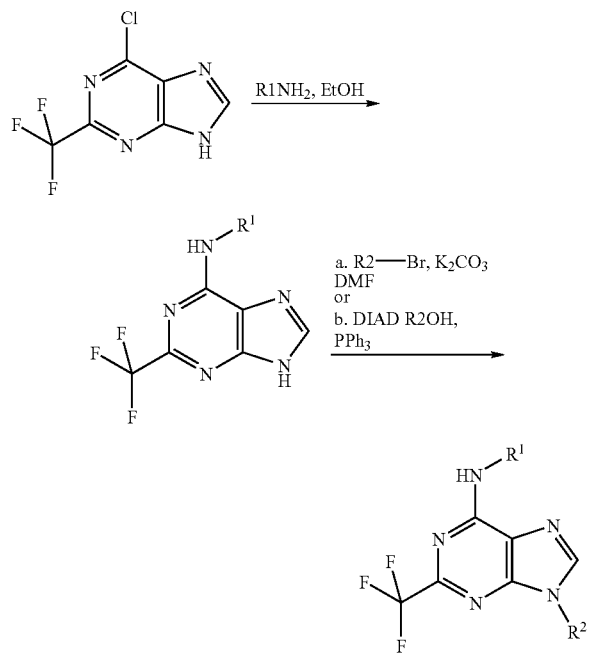

increased reaction temperature, e.g., 60° C. to 150° C., can be used to enhance reaction rates or reaction yields. Alternatively, reaction of 6-N-substituted adenines under Mitsunobu conditions with an alkyl alcohol, cycloalkyl alcohol, arylalkyl alcohol, heteroaryl alcohol, or cycloalkylalkyl alcohol provides 9-substituted 6-N-substituted adenines of formulas I-III.

6-N-Substituted-9-aryl- and 9-heteroaryl-adenines may be synthesized by methods common to the art, such as by reaction of a 4,6-dichloro-5-aminopyrimidine with an appropriately substituted aniline or heteroarylamine as described by J. L. Kelley et. al., *J. Med. Chem.*, 1997, 40, 3207 to produce 4-arylamino or 4-heteroarylamino-6-chloropyrimidines. Cyclization by treating with triethylorthoformate in the presence of an acid catalyst (e.g. ethylsulfonic acid) provides 6-choro-9-aryl- or 9-heteroaryl-purines, which can be derivatized at the 6-N-position as described above to provide adenine derivatives of formulas I-III.

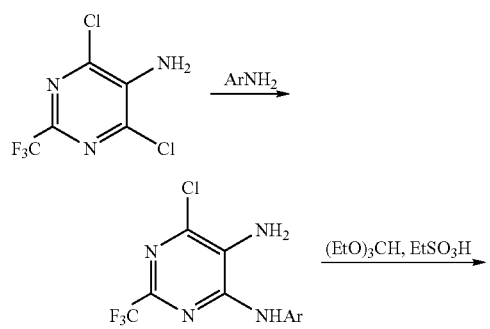

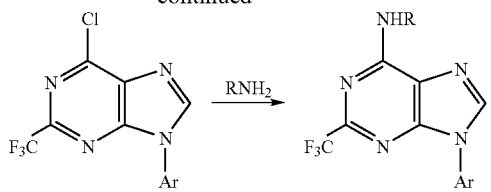

Alternatively, 6-N-substituted adenines may undergo a coupling reaction with arylboronic acids or heteroarylboronic acids in the presence of a base (e.g. triethylamine, pyridine, N—

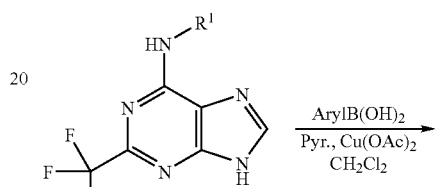

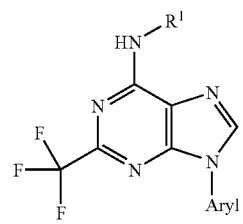

methylmorpholine), a copper catalyst (e.g., Cu(OAc)$_2$), and a polar aprotic solvent (e.g. dichloromethane, 1,4-dioxane, THF, DMF, CH$_3$CN) in a modoified manner as described previously for the N-arylation of imidazole and pyrazole (see, P. Y. S. Lam et. al. Tetrahedron Lett. 1998, 39, 2941-2944) to generate 9-aryl- or 9-heteroaryl-adenines of formulas I-III. Thus, preferably, the use of triethylamine, rather than pyridine, as a base, and warming to 50-60° C. in CH$_3$CN, rather than stirring at room temperature in CH$_2$Cl$_2$, provides the novel compounds.

Alternatively, certain halogenated aryl and heteroaryl substrates can undergo aromatic nucleophilic substitution reaction with 6-(substituted)amino-2-trifluoromethylpurine in a polar aprotic solvent (e.g., DMF or DMSO) using a base (e.g., cesium carbonate) to provide target 9-aryl or 9-heteroarylpurines.

Many of these synthetic procedures are described more fully in the examples below.

One of ordinary skill in the art will recognize that some of the compounds of Formulas I-III can exist in different geometrical isomeric forms. In addition, some of the compounds of the present invention possess one or more asymmetric carbon atoms and are thus capable of existing in the form of optical isomers, as well as in the form of racemic or nonracemic mixtures thereof, and in the form of diastereomers and diastereomeric mixtures inter alia. All of these compounds, including cis isomers, trans isomers, diastereomic mixtures, racemates, nonracemic mixtures of enantiomers, and substantially pure and pure enantiomers, are within the scope of the present invention. Substantially pure enantiomers contain no more than 5% w/w of the corresponding opposite enantiomer, preferably no more than 2%, most preferably no more than 1%.

The optical isomers can be obtained by resolution of the racemic mixtures according to conventional processes, for example, by the formation of diastereoisomeric salts using an optically active acid or base or formation of covalent diastereomers. Examples of appropriate acids are tartaric, diacetyltartaric, dibenzoyltartaric, ditoluoyltartaric and camphorsulfonic acid. Mixtures of diastereoisomers can be separated into their individual diastereomers on the basis of their physical and/or chemical differences by methods known to those skilled in the art, for example, by chromatography or fractional crystallization. The optically active bases or acids are then liberated from the separated diastereomeric salts. A different process for separation of optical isomers involves the use of chiral chromatography (e.g., chiral HPLC columns), with or without conventional derivation, optimally chosen to maximize the separation of the enantiomers. Suitable chiral HPLC columns are manufactured by Diacel, e.g., Chiracel OD and Chiracel OJ among many others, all routinely selectable. Enzymatic separations, with or without derivitization, are also useful. The optically active compounds of Formulae I-III can likewise be obtained by chiral syntheses utilizing optically active starting materials.

The present invention also relates to useful forms of the compounds as disclosed herein, such as pharmaceutically acceptable salts and prodrugs of all the compounds of the present invention. Pharmaceutically acceptable salts include those obtained by reacting the main compound, functioning as a base, with an inorganic or organic acid to form a salt, for example, salts of hydrochloric acid, sulfuric acid, phosphoric acid, methane sulfonic acid, camphor sulfonic acid, oxalic acid, maleic acid, succinic acid and citric acid. Pharmaceutically acceptable salts also include those in which the main compound functions as an acid and is reacted with an appropriate base to form, e.g., sodium, potassium, calcium, mangnesium, ammonium, and choline salts. Those skilled in the art will further recognize that acid addition salts of the claimed compounds may be prepared by reaction of the compounds with the appropriate inorganic or organic acid via any of a number of known methods. Alternatively, alkali and alkaline earth metal salts are prepared by reacting the compounds of the invention with the appropriate base via a variety of known methods.

The following are further examples of acid salts that can be obtained by reaction with inorganic or organic acids: acetates, adipates, alginates, citrates, aspartates, benzoates, benzenesulfonates, bisulfates, butyrates, camphorates, digluconates, cyclopentanepropionates, dodecylsulfates, ethanesulfonates, glucoheptanoates, glycerophosphates, hemisulfates, heptanoates, hexanoates, fumarates, hydrobromides, hydroiodides, 2-hydroxy-ethanesulfonates, lactates, maleates, methanesulfonates, nicotinates, 2-naphthalenesulfonates, oxalates, palmoates, pectinates, persulfates, 3-phenylpropionates, picrates, pivalates, propionates, succinates, tartrates, thiocyanates, tosylates, mesylates and undecanoates.

Preferably, the salts formed are pharmaceutically acceptable for administration to mammals. However, pharmaceutically unacceptable salts of the compounds are suitable as intermediates, for example, for isolating the compound as a salt and then converting the salt back to the free base compound by treatment with an alkaline reagent. The free base can then, if desired, be converted to a pharmaceutically acceptable acid addition salt.

The compounds of the invention can be administered alone or as an active ingredient of a formulation. Thus, the present invention also includes pharmaceutical compositions of compounds of Formula I containing, for example, one or more pharmaceutically acceptable carriers.

Numerous standard references are available that describe procedures for preparing various formulations suitable for administering the compounds according to the invention. Examples of potential formulations and preparations are contained, for example, in the Handbook of Pharmaceutical Excipients, American Pharmaceutical Association (current edition); Pharmaceutical Dosage Forms: Tablets (Lieberman, Lachman and Schwartz, editors) current edition, published by Marcel Dekker, Inc., as well as Remington's Pharmaceutical Sciences (Arthur Osol, editor), 1553-1593 (current edition).

In view of their high degree of PDE4 inhibition, the compounds of the present invention can be administered to anyone requiring or desiring PDE4 inhibition, and/or enhancement of cognition. Administration may be accomplished according to patient needs, for example, orally, nasally, parenterally (subcutaneously, intraveneously, intramuscularly, intrasternally and by infusion), by inhalation, rectally, vaginally, topically, locally, transdermally, and by ocular administration.

Various solid oral dosage forms can be used for administering compounds of the invention including such solid forms as tablets, gelcaps, capsules, caplets, granules, lozenges and bulk powders. The compounds of the present invention can be administered alone or combined with various pharmaceutically acceptable carriers, diluents (such as sucrose, mannitol, lactose, starches) and excipients known in the art, including but not limited to suspending agents, solubilizers, buffering agents, binders, disintegrants, preservatives, colorants, flavorants, lubricants and the like. Time release capsules, tablets and gels are also advantageous in administering the compounds of the present invention.

Various liquid oral dosage forms can also be used for administering compounds of the invention, including aqueous and non-aqueous solutions, emulsions, suspensions, syrups, and elixirs. Such dosage forms can also contain suitable inert diluents known in the art such as water and suitable excipients known in the art such as preservatives, wetting agents, sweeteners, flavorants, as well as agents for emulsifying and/or suspending the compounds of the invention. The compounds of the present invention may be injected, for example, intravenously, in the form of an isotonic sterile solution. Other preparations are also possible.

Suppositories for rectal administration of the compounds of the present invention can be prepared by mixing the compound with a suitable excipient such as cocoa butter, salicylates and polyethylene glycols. Formulations for vaginal administration can be in the form of a pessary, tampon, cream, gel, paste, foam, or spray formula containing, in addition to the active ingredient, such suitable carriers as are known in the art.

For topical administration the pharmaceutical composition can be in the form of creams, ointments, liniments, lotions, emulsions, suspensions, gels, solutions, pastes, powders, sprays, and drops suitable for administration to the skin, eye, ear or nose. Topical administration may also involve transdermal administration via means such as transdermal patches.

Aerosol formulations suitable for administering via inhalation also can be made. For example, for treatment of disorders of the respiratory tract, the compounds according to the invention can be administered by inhalation in the form of a powder (e.g., micronized) or in the form of atomized solutions or suspensions. The aerosol formulation can be placed into a pressurized acceptable propellant.

The compounds can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below its usual dosage range.

The present invention further includes methods of treatment that involve inhibition of PDE4 enzymes. Thus, the present invention includes methods of selective inhibition of PDE4 enzymes in animals, e.g., mammals, especially humans, wherein such inhibition has a therapeutic effect, such as where such inhibition may relieve conditions involving neurological syndromes, such as the loss of memory, especially long-term memory. Such methods comprise administering to an animal in need thereof, especially a mammal, most especially a human, an inhibitory amount of a compound, alone or as part of a formulation, as disclosed herein.

The condition of memory impairment is manifested by impairment of the ability to learn new information and/or the inability to recall previously learned information. Memory impairment is a primary symptom of dementia and can also be a symptom associated with such diseases as Alzheimer's disease, schizophrenia, Parkinson's disease, Huntington's disease, Pick's disease, Creutzfeld-Jakob disease, HIV, cardiovascular disease, and head trauma as well as age-related cognitive decline.

Dementias are diseases that include memory loss and additional intellectual impairment separate from memory. The present invention includes methods for treating patients suffering from memory impairment in all forms of dementia. Dementias are classified according to their cause and include: neurodegenerative dementias (e.g., Alzheimer's, Parkinson's disease, Huntington's disease, Pick's disease), vascular (e.g., infarcts, hemorrhage, cardiac disorders), mixed vascular and Alzheimer's, bacterial meningitis, Creutzfeld-Jacob Disease, multiple sclerosis, traumatic (e.g., subdural hematoma or traumatic brain injury), infectious (e.g., HIV), genetic (down syndrome), toxic (e.g., heavy metals, alcohol, some medications), metabolic (e.g., vitamin B12 or folate deficiency), CNS hypoxia, Cushing's disease, psychiatric (e.g., depression and schizophrenia), and hydrocephalus.

The present invention includes methods for dealing with memory loss separate from dementia, including mild cognitive impairment (MCI) and age-related cognitive decline. The present invention includes methods of treatment for memory impairment as a result of disease. In another application, the invention includes methods for dealing with memory loss resulting from the use of general anesthetics, chemotherapy, radiation treatment, post-surgical trauma, and therapeutic intervention.

The compounds may be used to treat psychiatric conditions including schizophrenia, bipolar or manic depression, major depression, and drug addiction and morphine dependence. These compounds may enhance wakefulness. PDE4 inhibitors can be used to raise cAMP levels and prevent neurons from undergoing apoptosis. PDE4 inhibitors are also known to be anti-inflammatory. The combination of anti-apoptotic and anti-inflammatory properties make these compounds useful to treat neurodegeneration resulting from any disease or injury, including stroke, spinal cord injury, neurogenesis, Alzheimer's disease, multiple sclerosis, amylolaterosclerosis (ALS), and multiple systems atrophy (MSA).

Thus, in accordance with a preferred embodiment, the present invention includes methods of treating patients suffering from memory impairment due to, for example, Alzheimer's disease, schizophrenia, Parkinson's disease, Huntington's disease, Pick's disease, Creutzfeld-Jakob disease, depression, aging, head trauma, stroke, CNS hypoxia, cerebral senility, multiinfarct dementia and other neurological conditions including acute neuronal diseases, as well as HIV and cardiovascular diseases, comprising administering an effective amount of a compound according to Formula (I) or (I') or pharmaceutically acceptable salts thereof.

The compounds of the present invention can also be used in a method of treating patients suffering from disease states characterized by decreased NMDA function, such as schizophrenia. The compounds can also be used to treat psychosis characterized by elevated levels of PDE 4, for example, various forms of depression, such as manic depression, major depression, and depression associated with psychiatric and neurological disorders.

As mentioned, the compounds of the invention also exhibit anti-inflammatory activity. As a result, the inventive compounds are useful in the treatment of a variety of allergic and inflammatory diseases, particularly disease states characterized by decreased cyclic AMP levels and/or elevated phosphodiesterase 4 levels. Thus, in accordance with a farther embodiment of the invention, there is provided a method of treating allergic and inflammatory disease states, comprising administering an effective amount of a compound according to Formulae (I) or (I') or a pharmaceutically acceptable salt thereof. Such disease states include: asthma, chronic bronchitis, chronic obstructive pulmonary disease (COPD), atopic dermatitis, urticaria, allergic rhinitis, allergic conjunctivitis, vernal conjunctivitis, esoniophilic granuloma, psoriasis, inflammatory arthritis, rheumatoid arthritis, septic shock, ulcerative colitis, Crohn's disease, reperfusion injury of the myocardium and brain, chronic glomerulonephritis, endotoxic shock, adult respiratory distress syndrome, cystic fibrosis, arterial restenosis, artherosclerosis, keratosis, rheumatoid spondylitis, osteoarthritis, pyresis, diabetes mellitus, pneumoconiosis, chronic obstructive airways disease, chronic obstructive pulmonary disease, toxic and allergic contact eczema, atopic eczema, seborrheic eczema, lichen simplex, sunburn, pruritis in the anogenital area, alopecia areata, hypertrophic scars, discoid lupus erythematosus, systemic lupus erythematosus, follicular and wide-area pyodermias, endogenous and exogenous acne, acne rosacea, Beghet's disease, anaphylactoid purpura nephritis, inflammatory bowel disease, leukemia, multiple sclerosis, gastrointestinal diseases, autoimmune diseases and the like.

PDE4 inhibitors for treating asthma, chronic bronchitis, psoriasis, allergic rhinitis, and other inflammatory diseases, and for inhibiting tumor necrosis factor are known within the art. See, e.g., WO 98/58901, JP11-18957, JP 10-072415, WO 93/25517, WO 94/14742, U.S. Pat. Nos. 5,814,651, and 5,935,9778. These references also describe assays for determining PDE4 inhibition activity, and methods for synthesizing such compounds. The entire disclosures of these documents are hereby incorporated by reference.

PDE4 inhibitors may be used to prevent or ameliorate osteoporosis, as an antibiotic, for treatment of cardiovascular disease by mobilizing cholesterol from atherosclerotic lesions, to treat rheumatoid arthritis (RA), for long-term inhibition of mesenchymal-cell proliferation after transplantation, for treatment of urinary obstruction secondary to benign prostatic hyperplasia, for suppression of chemotaxis and reduction of invasion of colon cancer cells, for treatment of B cell chronic lymphocytic leukemia (B-CLL), for inhibition of uterine contractions, to attenuate pulmonary vascular ischemia-reperfusion injury (IRI), for corneal hydration, for inhibition of IL-2R expression and thereby abolishing HIV-1 DNA nuclear import into memory T cells, for augmentation of glucose-induced insulin secretion, in both the prevention and treatment of colitis, and to inhibit mast cell degranulation.

The compounds of the present invention can be administered as the sole active agent or in combination with other pharmaceutical agents such as other agents used in the treatment of cognitive impairment and/or in the treatment of psychosis, e.g., other PDE4 inhibitors, calcium channel blockers, chloinergic drugs, adenosine receptor modulators, amphakines NMDA-R modulators, mGluR modulators, and cholinesterase inhibitors (e.g., donepezil, rivastigimine, and glanthanamine). In such combinations, each active ingredient can be administered either in accordance with their usual dosage range or a dose below their usual dosage range.

The dosages of the compounds of the present invention depend upon a variety of factors including the particular syndrome to be treated, the severity of the symptoms, the route of administration, the frequency of the dosage interval, the particular compound utilized, the efficacy, toxicology profile, pharmacokinetic profile of the compound, and the presence of any deleterious side-effects, among other considerations.

The compounds of the invention are typically administered at dosage levels and in a mammal customary for PDE4 inhibitors such as those known compounds mentioned above. For example, the compounds can be administered, in single or multiple doses, by oral administration at a dosage level of, for example, 0.01-100 mg/kg/day, preferably 0.1-70 mg/kg/day, especially 0.5-10 mg/kg/day. Unit dosage forms can contain, for example, 0.1-50 mg of active compound. For intravenous administration, the compounds can be administered, in single or multiple dosages, at a dosage level of, for example, 0.001-50 mg/kg/day, preferably 0.001-10 mg/kg/day, especially 0.01-1 mg/kg/day. Unit dosage forms can contain, for example, 0.1-10 mg of active compound.

In carrying out the procedures of the present invention it is of course to be understood that reference to particular buffers, media, reagents, cells, culture conditions and the like are not intended to be limiting, but are to be read so as to include all related materials that one of ordinary skill in the art would recognize as being of interest or value in the particular context in which that discussion is presented. For example, it is often possible to substitute one buffer system or culture medium for another and still achieve similar, if not identical, results. Those of skill in the art will have sufficient knowledge of such systems and methodologies so as to be able, without undue experimentation, to make such substitutions as will optimally serve their purposes in using the methods and procedures disclosed herein.

The present invention will now be further described by way of the following non-limiting examples. In applying the disclosure of these examples, it should be kept clearly in mind that other and different embodiments of the methods disclosed according to the present invention will no doubt suggest themselves to those of skill in the relevant art.

In the foregoing and in the following examples, all temperatures are set forth uncorrected in degrees Celsius; and, unless otherwise indicated, all parts and percentages are by weight.

The entire disclosures of all applications, patents and publications, cited above and below, are hereby incorporated by reference.

EXAMPLE 1

1,9-Dihydro-2-trifluoromethyl-6H-purin-6-one
(Kelly, J. L.; Linn, J. A.; Selway, J. W. T., *J. Med. Chem.*, 1989, 32, 1757-1763)

A 1 L round-bottom flask (three neck) containing 340 g of trifluoroacetamide was heated in an oil bath at 110° C. After the trifluoroacetamide melted, 50 g of 5-aminoimidazole-4-carboxamide-HCl was added. The mixture was warmed to reflux (bath temp 160 to 165° C.) for 4 hours, cooled to room temperature, and the rocky solid was triturated with 1 L of ether. The ether was decanted off and the remaining solid was warmed until melted and 200 mL of ether was introduced by a dropping-funnel through a water-cooled condenser. The mixture was cooled to room temperature and an additional 200 mL of ether was added with stirring. The solid was removed by filtration, triturated with 3×500 mL of ether, washed with 200 mL of $H_2O$, and filtered to provide 89 g of crude product. The product was treated with 3 L of MeOH and 9 g of activated carbon, warmed to reflux for 20 minutes, filtered through a pad of celite, and concentrated to a volume of 2.5 L. The material was warmed to dissolve all the precipitate that formed and then cooled slowly to room temperature. The crystalline material was isolated by filtration and dried in vacuo to provide 41 g of the desired hypoxanthine as a white solid. $^1$H NMR (DMSO-$d_6$) δ 8.34 (s, 1H), 7.18 (bs, 2H). MS (ES+), 205.0 (100%, M+H).

EXAMPLE 2

6-Chloro-2-trifluoromethylpurine

A mixture of 15 g (73 mmol) of 2-trifluoromethylhypoxanthine and 300 mL of $CHCl_3$ was warmed to reflux and treated with a solution of 26.7 mL (366 mmol) $SOCl_2$ and 28.3 mL (366 mmol) DMF. The reaction was maintained at reflux for 1.5 h, cooled to room temperature, and poured into 1.2 L of ice-water. The organic layer was separated and washed with 2×300 mL of $H_2O$. The pH of the combined aqueous phases was adjusted to 7 with saturated $NaHCO_3$ and extracted with 3×1.2 L of ether. The combined ether and chloroform extracts were dried ($MgSO_4$) and concentrated to dryness to give 7.4 g of crude product. $^1$H NMR (DMSO-$d_6$) δ 14.45 (bs, 1H), 8.95 (s, 1H). MS (ES+) 222.96 (100%, M+H).

EXAMPLE 3

6-Chloro-9-(2-fluorobenzyl)-2-trifluoromethylpurine

A mixture of 5 g (22.5 mmol) of 6-chloro-2 trifluoromethylpurine, 4.05 g (29.4 mmol) of anhydrous $K_2CO_3$, 56 mL of dry DMF, and 3.55 mL (29.4 mmol) of 2-fluorobenzyl bromide was stirred at room temperature for 16 h. The reaction mixture was poured into 50 mL of ice-water and the pH of the solution was adjusted to 5 or 6 with acetic acid.

The mixture was extracted with 3×300 mL of ether and the combined organic fractions were washed with 3×350 mL of H₂O, 300 mL of brine, dried (Na₂SO₄), and concentrated in vacuo to provide a yellow oil. Purification by chromatography over silica gel using a gradient elution going from 20% EtOAc in hexanes to 50% EtOAc in hexanes provided 3.5 g (47% yield) of the desired 9-isomer (first to elute) and 1.97 g (27% yield) of the 7-isomer. ¹H NMR (CDCl₃) δ 8.33 (s, 1H), 7.50-7.47 (m, 1H), 7.40-7.38 (m, 1H), 7.20-7.11 (m, 2H), 5.56 (s, 2H).

EXAMPLE 4

6-Cyclopropylamino-9-(2-fluorobenzyl)-2-trifluoromethylpurine

A mixture of 100 mg (0.30 mmol) of 6-chloro-9-(2-fluorobenzyl)-2-trifluoromethylpurine, 1 mL (14 mmol) of aminocyclopropane, and 5 mL of EtOH were stirred at room temperature for 16 hours. The reaction mixture was concentrated in vacuo and the residue was dissolved in CH₂Cl₂, washed with 2×5 mL H₂O, 5 mL brine, dried (Na₂SO₄), and concentrated. Chromatography over silica gel using 33% EtOAc in hexanes as eluant provided 102 mg (97% yield) of the desired product. M.P. 118.5-119.0° C.; ¹H NMR (CDCl₃) δ 7.892 (s, 1H), 7.50-7.39 (m, 1H), 7.37-7.29 (m, 1H), 7.18-7.05 (m, 2H), 5.95 (bs, 1H), 5.44 (s, 2H), 0.94-0.91 (m, 2H), 0.65-0.64 (m, 2H).

To obtain the methansulphonate salt (mesylate salt), 4 ml of 0.1N CH₃SO₃H in EtOAc was added to a solution of 145 mg (0.4 mmol) 6-cyclopropylamino-9-(2-fluorobenzyl)-2-trifluoromethylpurine in EtOAc. Then, 1 ml of hexane was added to a warm solution and the resultant mixture was allowed to crystallize (within a refrigerator). The solid was collected to give 148 mg of the mesylate salt. The salt was relatively insoluble in H₂O. M.p. 167.5-169.0 C; m.p. 114-118 C for free base.

The following compounds were prepared in a similar fashion as described above.
a. 6-Methylamino-9-(2-fluorobenzyl)-2-trifluoromethylpurine
b. 6-Ethylamino-9-(2-fluorobenzyl)-2-trifluoromethylpurine
c. 6-Amino-9-(2-fluorobenzyl)-2-trifluoromethylpurine
d. 6-N-Cyclopropylmethylamino-9-(2-fluorobenzyl)-2-trifluoromethylpurine
e. 6-[1-(2-Hydroxy)ethyl]amino-9-(2-fluorobenzyl)-2-trifluoromethylpurine
f. 6-Cyclopentylamino-9-(2-fluorobenzyl)-2-trifluoromethylpurine
g. 6-Cyclohexylamino-9-(2-fluorobenzyl)-2-trifluoromethylpurine
h. 6-Isopropylamino-9-(2-fluorobenzyl)-2-trifluoromethylpurine

EXAMPLE 5

6-Cyclopropylamino-2-trifluoromethylpurine

A mixture of 12 g (54 mmol) of 6-chloro-2-trifluoromethylpurine, 30 g (540 mmol) of cyclopropylamine and 250 mL of ethanol was stirred at room temperature for 4.5 days leaving a white solid. The mixture was concentrated in vacuo to dryness, 215 mL of H₂O was added and the mixture was stirred for 1 hour. The product was collected by filtration and after drying (vacuum oven, 50° C., 5 hours) 8.1 g of product was obtained, 62% yield. M.P. 260° C. (dec.); ¹H NMR (CD₃OD) δ 8.18 (s, 1H), 3.30 (bs, 1H), 0.904 (m, 2H), 0.67 (m, 2H).

The following compounds are prepared in a similar manner:
a. 6-Methylamino-2-trifluuoromethylpurine
b. 6-Cyclopentylamino-2-trifluoromethylpurine

EXAMPLE 6

6-Cyclopropylamino-9-(2-fluorobenzyl)-2-trifluoromethylpurine

To a nitrogen flushed tube with stir bar was added 25 mg (0.13 mmol) of 2-fluorobenzyl bromide, 0.7 mL of anhydrous DMF, 18 mg (0.13 mmol) of K₂CO₃ and 0.5 mL (0.10 mmol) of 0.2M 6-cyclopropylamino-2-trifluoromethyladenine in anhydrous DMF. The reaction was stirred at room temperature for 18 hours, quenched with 2 mL of ice water and the pH was adjusted to between 5 and 6 with acetic acid. The aqueous mixture was extracted with 10 mL of ether and the ether fraction was washed with 3 mL of H₂O, 3 mL of brine, dried (MgSO₄) and concentrated to dryness in vacuo. M.P. 118.5-119.0° C.; ¹H NMR (CDCl₃) δ 7.892 (s, 1H), 7.50-7.39 (m, 1H), 7.37-7.29 (m, 1H), 7.18-7.05 (m, 2H), 5.95 (bs, 1H), 5.44 (s, 2H), 0.94-0.91 (m, 2H), 0.65-0.64 (m, 2H).

The following compounds were prepared in a similar manner.
a. 6-Cyclopropylamino-9-(3-methoxybenzyl)-2-trifluoromethylpurine
b. 6-Cyclopropylamino-9-(3-chlorobenzyl)-2-trifluoromethylpurine
c. 6-Cyclopropylamino-9-(3-nitrobenzyl)-2-trifluoromethylpurine
d. 6-Cyclopropylamino-9-(4-cyanobenzyl)-2-trifluoromethylpurine
e. 6-Cyclopropylamino-9-(4-trifluoromethylbenzyl)-2-trifluoromethylpurine
f. 6-Cyclopropylamino-9-(3,4-dichlorobenzyl)-2-trifluoromethylpurine
g. 6-Cyclopropylamino-9-(4-chlorobenzyl)-2-trifluoromethylpurine
h. 6-Cyclopropylamino-9-(3,4-difluorobenzyl)-2-trifluoromethylpurine
i. 6-Cyclopropylamino-9-(3-pyridylmethyl)-2-trifluoromethylpurine
j. 6-Cyclopropylamino-9-[α-(2-chloroacetophenone)]-2-trifluoromethylpurine
k. 6-Cyclopropylamino-9-[α-(4-methoxyacetophenone)]-2-trifluoromethylpurine
l. 6-Cyclopropylamino-9-(3,5-difluorobenzyl)-2-trifluoromethylpurine
m. 6-Cyclopropylamino-9-ethyl-2-trifluoromethylpurine
n. 6-Cyclopropylamino-9-[α-(4-methylacetophenone)]-2-trifluoromethylpurine
o. 6-Cyclopropylamino-9-(3-trifluoromethylbenzyl)-2-trifluoromethylpurine
p. 6-Cyclopropylamino-9-(3,5-bistrifluoromethylbenzyl)]-2-trifluoromethylpurine
q. 6-Cyclopropylamino-9-(4-methylsulfonylbenzyl)]-2-trifluoromethylpurine
r. 6-Cyclopropylamino-9-(4-nitrobenzyl)-2-trifluoromethylpurine
s. 6-Cyclopropylamino-9-(4-tert-butylbenzyl)-2-trifluoromethylpurine t. 6-Cyclopropylamino-9-(1-pentan-3-one)-2-trifluoromethylpurine
u. 6-Cyclopropylamino-9-[α-(2-methoxyacetophenone)]-2-trifluoromethylpurine
v. 6-Cyclopropylamino-9-[α-(4-cyanoacetophenone)]-2-trifluoromethylpurine
w. 6-Cyclopropylamino-9-[α-(3-chloroacetophenone)]-2-trifluoromethylpurine
x. 6-Cyclopropylamino-9-[α-(3-methoxyacetophenone)]-2-trifluoromethylpurine
y. 6-Cyclopropylamino-9-[α-(4-chloroacetophenone)]-2-trifluoromethylpurine
z. 6-Cyclopropylamino-9-[α-(3,4-dichloroacetophenone)-2-trifluoromethylpurine
aa. 6-Cyclopropylamino-9-(4-pyridylmethyl)-2-trifluoromethylpurine
bb. 6-Cyclopropylamino-9-(2-pyridylmethyl)-2-trifluoromethylpurine
cc. 6-Cyclopropylamino-9-(4-ethylbenzyl-2-trifluoromethylpurine
dd. 6-Cyclopropylamino-9-(3,4-dimethoxybenzyl)-2-trifluoromethylpurine
ee. 6-Cyclopropylamino-9-(2,4-dichlorobenzyl)-2-trifluoromethylpurine
ff. 6-Cyclopropylamino-9-(2,3-dichlorobenzyl)-2-trifluoromethylpurine
gg. 6-Cyclopropylamino-9-(3,4-ethylenedioxybenzyl)-2-trifluoromethylpurine
hh. 6-Cyclopropylamino-9-(3,4-methylenedioxybenzyl)-2-trifluoromethylpurine
ii. 6-Cyclopropylamino-9-(4-isopropylbenzyl)-2-trifluoromethylpurine
jj. 6-Cyclopropylamino-9-(3-thienylmethyl)-2-trifluoromethylpurine
kk. 6-Cyclopropylamino-9-(2-thienylmethyl)-2-trifluoromethylpurine
ll. 6-Cyclopropylamino-9-(2-furylmethyl)-2-trifluoromethylpurine
mm. 6-Cyclopropylamino-9-(3-furylmethyl)-2-trifluoromethylpurine
nn. 6-Cyclopropylamino-9-[-(2-(2-chlorophlenyl)ethyl)]-2-trifluoromethylpurine
oo. 6-Cyclopropylamino-9-[1-(2-(2-fluorophenyl)ethyl)]-2-trifluorometuylpurine
pp. 6-Cyclopropylamino-9-[1-(2-(2-toluyl)ethyl)]-2-trifluoromethylpurine
qq. 6-Cyclopropylamino-9-[1-(2-(3-chlorophenyl)ethyl)]-2-trifluoromethylpurine
rr. 6-Cyclopropylamino-9-[1-(2-(3-toluyl)ethyl)]-2-trifluoromethylpurine
ss. 6-Cyclopropylamino-9-[1-(2-(3-methoxyphenyl)ethyl)]-2-trifluoromethylpurine
tt. 6-Cyclopropylamino-9-[1-(2-(4-chlorophenyl)ethyl)]-2-trifluoromethylpurine
uu. 6-Cyclopropylamino-9-[1-(2-(4-toulyl)ethyl)]-2-trifluoromethylpurine
vv. 6-Cyclopropylamino-9-[1-(2-(4-methoxyphenyl)ethyl)]-2-trifluoromethylpurine
ww. 6-Cyclopropylamino-9-[1-(3-(2-methoxyphenyl)propyl)]-2-trifluoromethylpurine
xx. 6-Cyclopropylamino-9-[1-(3-(4-chlorophenyl)propyl)]-2-trifluoromethylpurine
yy. 6-Cyclopropylamino-9-[1-(3-(4-methoxyphenyl)propyl)]-2-trifluoromethylpurine
zz. 6-Cyclopropylamino-9-(3-benzyloxybenzyl)-2-trifluoromethylpurine
aaa. 6-Cyclopropylamino-9-(2,6-difluorobenzyl)-2-trifluoromethylpurine
bbb. 6-Cyclopropylamino-9-cyclopentyl-2-trifluoromethylpurine
ccc. 6-Cyclopropylamino-9-(1-propyl)-2-trifluoromethylpurine
ddd. 6-Cyclopropylamino-9-(2,3-difluorobenzyl)-2-trifluoromethylpurine
eee. 6-Cyclopropylamino-9-(4-fluorobenzyl)-2-trifluoromethylpurine
fff. 6-Cyclopropylamino-9-(2-chlorobenzyl)-2-trifluoromethylpurine
ggg. 6-Cyclopropylamino-9-(3-methylbenzyl)-2-trifluoromethylpurine
hhh. 6-Cyclopropylamino-9-(2-chloro-4-fluorobenzyl)-2-trifluoromethylpurine
iii. 6-Cyclopropylamino-9-[1-(2-methoxyethyl)]-2-trifluoromethylpurine
jjj. 6-Cyclopropylamino-9-(2-butyl)-2-trifluoromethylpurine
kkk. 6-Cyclopropylamino-9-(1-butyl)-2-trifluoromethylpurine
lll. 6-Cyclopropylamino-9-(2-methylbenzyl)-2-trifluoromethylpurine
mmm. 6-Cyclopropylamino-9-(2-fluorobenzyl)-2-trifluoromethylpurine
nnn. 6-Cyclopropylamino-9-(2,4-difluorobenzyl)-2-trifluoromethylpurine
ooo. 6-Cyclopropylamino-9-(2-nitrobenzyl)-2-trifluoromethylpurine
ppp. 6-Cyclopropylamino-9-benzyl-2-trifluoromethylpurine
qqq. 6-Cyclopropylamino-9-(2-propyl)-2-trifluoromethylpurine
rrr. 6-Cyclopropylamino-9-(2-trifluromethylbenzyl)-2-trifluoromethylpurine
sss. 6-Cyclopropylamino-9-(3-fluorobenzyl)-2-trifluoromethylpurine
ttt. 6-Cyclopropylamino-9-(4-phenylbenzyl)-2-trifluoromethylpurine
uuu. 6-Cyclopropylamino-9-(2-phenylbenzyl)-2-trifluoromethylpurine
vvv. 6-Cyclopropylamino-9-cyclohexyl-2-trifluoromethylpurine
www. 6-Cyclopropylamino-9-cycloheptyl-2-trifluoromethylpurine The following compounds can be prepared in a manner similar to that described in Example 6 using cesium carbonate rather than potassium carbonate:
a. 6-Cyclopropylamino-9-(2,6-dichloro-4-pyridylmethyl)-2-trifluoromethylpurine
b. 6-Cyclopropylamino-9-(4-methoxybenzyl)-2-trifluoromethylpurine
c. 6-Cyclopropylamino-9-(3-nitrobenzyl)-2-trifluoromethylpurine
d. 6-Cyclopropylamino-9-(2-pyrimidyl)-2-trifluoromethylpurine
e. 6-Cyclopropylamino-9-(4-(2-diethylamino)pyrimidyl)-2-trifluoromethylpurine
f. 6-Cyclopropylamino-9-(4-(2-chloro)pyrimidyl)-2-trifluoromethylpurine
g. 6-Cyclopropylamino-9-(4-(2-methylthio)pyrimidyl)-2-trifluoromethylpurine The following compounds can be prepared in a manner similar to that above using 6-N-methylamino-2-trifluoromethylpurine as a starting material:
a. 6-N-methylamino-9-cyclopentyl-2-trifluoromethylpurine
b. 6-N-methylamino-9-cycloheptyl-2-trifluoromethylpurine The following compound can be prepared in a manner similar to that described above using 6-N-cyclopentylamino-2-trifluoromethylpurine as a starting material:
a. 6-N-cyclopentylamino-9-methyl-2-trifluoromethylpurine.

EXAMPLE 7

6-Cyclopropylamino-9-(3-aminophenyl)-2-trifluoromethylpurine

A mixture of 6-Cyclopropylamino-9-(3-nitrophenyl)-2-trifluoromethylpurine (0.1 mmol), palladium on active carbon (0.001 mol) methanol (50 ml) and acetic acid (3 ml) was shaken under 30 psi hydrogen. After 5 hours, the reaction mixture was filtered through celite and the filtrate was concentrated in vacuo. The resultant residue was dissolved in 30 ml of ethyl acetate, washed with 30 mL of aqueous 5% sodium bicarbonate, concentrated and purified by chromatography over $SiO_2$ to give the amino product in quantitative yield. $^1$H NMR (300 MHz, $CDCl_3$) □ 8.10 (s, 1H), 7.27 (t, J=8.1 Hz, 1H), 7.05 (s, 1H), 6.98 (d, J=8.1 Hz, 1H), 6.70 (d, J=8.1 Hz, 1H), 6.35(b, 1H), 3.18 (b, 1H), 0.91 (m, 2H), 0.69 (m, 2H).

The following compounds can be made in a similar manner:

6-Cyclopropylamino-9-(3-aminobenzyl)-2-trifluoromethylpurine

EXAMPLE 8

6-Cyclopropylamino-9-cyclopentyl-2-trifluoromethylpurine (Pragnacharyulu, P. V. P.; Varkhedkar, V.; Curtis, M. A.; Chang, I. F.; Abushanab, E., *J. Med. Chem.*, 2000, 43, 4694-4700).

To a solution of 20 mg (0.08 mmol) 6-cyclopropylamino-2-trifluoromethylpurine, 42 mg (0.16 mmol) of $PPh_3$, and 18 mg (0.21 mmol) cyclopentanol in THF under $N_2$ atmosphere with magnetic stirring, was added 48 mg (0.23 mmol) DIAD. The resulting mixture was stirred at room temperature for 16 hours, concentrated, taken up in 10 mL $H_2O$ and extracted with 2×15 mL of ether. The organic layer was combined and dried over ($MgSO_4$), concentrated in vacuo, and purified by chromatography over silica gel using 10% MeOH in $CH_2Cl_2$ to give the desired product. $^1$H NMR ($CDCl_3$) 7.92 (s, 1H), 6.01 (bs, 1H), 4.98 (p, 1H), 3.18 (bs, 1H), 2.36-2.25 (m, 2H), 2.03-1.79 (m, 6H), 0.86 (dd, 2H), 0.65 (dd, 2H).

The following compounds were prepared in a similar manner:
a. 6-Cyclopropylamino-9-cyclopentylmethyl-2-trifluoromethylpurine
b. 6-Cyclopropylamino-9-cyclopentylethyl-2-trifluoromethylpurine
c. 6-Cyclopropylamino-9-cyclopentylpropyl-2-trifluoromethylpurine
d. 6-Cyclopropylamino-9-(3-(1-ethyl-pyrrolidinyl)-2-trifluoromethylpurine
e. 6-Cyclopropylamino-9-(3-(1-ethyl-piperidinyl)-2-trifluoromethylpurine
f. 6-Cyclopropylamino-9-(2-(1-ethyl-piperidinyl)-2-trifluoromethylpurine
g. 6-Cyclopropylamino-9-(piperidin-1-ylethyl)-2-trifluoromethylpurine
h. 6-Cyclopropylamino-9-(2-(1-methyl-piperidinyl)-2-trifluoromethylpurine
i. 6-Cyclopropylamino-9-(5-oxo-(S)-pyrrolidin-3-yl)-2-trifluoromethylpurine
j. 6-Cyclopropylamino-9-(5-oxo-(R)-pyrrolidin-3-yl)-2-trifluoromethylpurine

EXAMPLE 9

6-Cyclopropylamino-9-(3,4-dimethoxyphenyl)-2-trifluoromethylpurine

A mixture of 6-cyclopropylamino-2-trifluoromethyladenine (46 mg, 0.2 mmol), 3,4-dimethoxyphenyl boronic acid (44 mg, 0.24 mmol), copper(II) acetate (36 mg, 0.2 mmol), triethylamine (1.0 mmol, 101 mg), anhydrous acetonitrile (4 ml) and molecular seives (~10 pellets) was stirred at 50-55° C. for 18 hours. Ethyl acetate (20 ml) was added and the solid was removed by filtration. The filtrate was washed with 20 ml of 5% sodium bicarbonate aqueous solution. Evaporation and chromatography over $SiO_2$ using hexane/ethylacetate/methanol (50:50:1) as elunt gave 7.9 mg of the title compound (yield 10%). $^1$H NMR (300 MHz, $CDCl_3$) δ 8.10 (s, 1H), 7.39 (s, 1H), 7.13 (d, J=8.7 Hz, 2H), 6.98 (d, J=8.7 Hz, 2H), 6.35(b, 1H), 3.93 (s, 3H), 3.90 (s, 3H), 3.18 (b, 1H), 0.91 (m, 2H), 0.69 (m, 2H)

The following compounds were prepared in a similar manner:
a. 6-Cyclopropylamino-9-(3,4-dimethoxyphenyl)-2-trifluoromethylpurine
b. 6-Cyclopropylamino-9-(3-methoxyphenyl)-2-trifluoromethylpurine
c. 6-Cyclopropylamino-9-(4-methoxyphenyl)-2-trifluoromethylpurine
d. 6-Cyclopropylamino-9-(3-nitrophenyl)-2-trifluoromethylpurine
e. 6-Cyclopropylamino-9-(2-methoxyphenyl)-2-trifluoromethylpurine
f. 6-Cyclopropylamino-9-(3-cyanophenyl)-2-trifluoromethylpurine
g. 6-Cyclopropylamino-9-(2,5-dimethoxphenyl)-2-trifluoromethylpurine
h. 6-Cyclopropylamino-9-(2,4-dimethoxypyrimidyl)-2-trifluoromethylpurine
i. 6-Cyclopropylamino-9-(2-methoxy-5-pyridyl)-2-trifluoromethylpurine
j. 6-Cyclopropylamino-9-(4-pyridyl)-2-trifluoromethylpurine
k. 6-Cyclopropylamino-9-(3-pyridyl)-2-trifluoromethylpurine
l. 6-Cyclopropylamino-9-(1-tert-butoxycarbonyl-pyrrol-2-yl)-2-trifluoromethylpurine
m. 6-Cyclopropylamino-9-(4-dimethylaminophenyl)-2-trifluoromethylpurine
n. 6-Methylamino-9-(2,4-dimethoxy-5-pyrimidyl)-2-trifluoromethylpurine
o. 6-Methylamino-9-(2-methoxyphenyl)-2-trifluoromethylpurine
p. 6-Methylamino-9-(4-methoxyphenyl)-2-trifluoromethylpurine
q. 6-Methylamino-9-(3-acetylphenyl)-2-trifluoromethylpurine
r. 6-Methylamino-9-(3-methoxyphenyl)-2-trifluoromethylpurine
s. 6-Methylamino-9-(3-nitrophenyl)-2-trifluoromethylpurine
t. 6-Cyclopropylamino-9-(3-furanyl)-2-trifluoromethylpurine u. 6-Cyclopropylamino-9-(4-ethoxyphenyl)-2-trifluoromethylpurine
v. 6-Cyclopropylamino-9-(2-ethoxyphenyl)-2-trifluoromethylpurine
w. 6-Cyclopropylamino-9-(3,4-methylenedioxyphenyl)-2-trifluoromethylpurine
x. 6-Cyclopropylamino-9-(3-ethoxyphenyl)-2-trifluoromethylpurine
y. 6Methylamino-9-(3,4-dimethoxyphenyl)-2-trifluoromethylpurine
z. 6-Cyclopropylamino-9-(3,5-dimethoxyphenyl)-2-trifluoromethylpurine
aa. 6-Cyclopropylamino-9-(2-methoxy-5-chlorophenyl)-2-trifluoromethylpurine
bb. 6-Cyclopropylamino-9-phenyl-2-trifluoromethylpurine
cc. 6-Cyclopropylamino-9-(2-fluorophenyl)-2-trifluoromethylpurine
dd. 6-Cyclopropylamino-9-(4-fluorophenyl)-2-trifluoromethylpurine
ee. 6-Cyclopropylamino-9-(4-chlorophenyl)-2-trifluoromethylpurine
ff. 6-Cyclopropylamino-9-(4-toluyl)-2-trifluoromethylpurine
gg. 6-Cyclopropylamino-9-(4-trifluoromethylphenyl)-2-trifluoromethylpurine
hh. 6-Cyclopropylamino-9-(3-thienyl)-2-trifluoromethylpurine
ii. 6-Cyclopropylamino-9-(3-trifluoromethylphenyl)-2-trifluoromethylpurine

EXAMPLE 10

In Vitro Measurement of Type 4 Phosphodiesterase Inhibition Activity

Human PDE4 was obtained from baculovirus-infected Sf9 cells that expressed the recombinant enzyme. The cDNA encoding hPDE-4D6 was subcloned into a baculovirus vector. Insect cells (Sf9) were infected with the baculovirus and cells were cultured until protein was expressed. The baculovirus-infected cells were lysed and the lysate was used as source of hPDE-4D6 enzyme. The enzyme was partially purified using a DEAE ion exchange chromatography. This procedure can be repeated using cDNA encoding other PDE-4 enzymes.

Assay:

Type 4 phosphodiesterases convert cyclic adenosine monophosphate (cAMP) to 5'-adenosine monophosphate (5'-AMP). Nucleotidase converts 5'-AMP to adenosine. Therefore the combined activity of PDE4 and nucleotidase converts cAMP to adenosine. Adenosine is readily separated from cAMP by neutral alumina columns. Phosphodiesterase inhibitors block the conversion of cAMP to adenosine in this assay; consequently, PDE4 inhibitors cause a decrease in adenosine.

Cell lysates (40 ul) expressing hPDE-4D6 were combined with 50 ul of assay mix and 10 ul of inhibitors and incubated for 12 min at room temperature. Final concentrations of assay components were: 0.4 ug enzyme, 10 mM Tris-HCl (pH 7.5), 10 mM $MgCl_2$, 3 uM cAMP, 0.002 U 5'-nucleotidase, and $3\times10^4$ cpm of [3H]cAMP. The reaction was stopped by adding 100 μl of boiling 5 mN HCl. An aliquot of 75 μl of reaction mixture was transferred from each well to alumina columns (Multiplate; Millipore). Labeled adenosine was eluted into an OptiPlate by spinning at 2000 rpm for 2 min; 150 μl per well of scintillation fluid was added to the OptiPlate. The plate was sealed, shaken for about 30 min, and cpm of [$^3$H]adenosine was determined using a Wallac Trilux®.

All test compounds are dissolved in 100% DMSO and diluted into the assay such that the final concentration of DMSO is 0.1%. DMSO does not affect enzyme activity at this concentration.

A decrease in adenosine concentration is indicative of inhibition of PDE activity. $pIC_{50}$ values were determined by screening 6 to 12 concentrations of compound ranging from 0.1 nM to 10,000 nM and then plotting drug concentration versus $^3$H-adenosine concentration. Nonlinear regression software (Assay Explorer®) was used to estimate $pIC_{50}$ values.

EXAMPLE 11

Passive Avoidance in Rats, an in vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). The apparatus (Model E10-16SC, Coulbourn Instruments, Allentown, Pa.) consisted of a two-compartment chamber with an illuminated compartment connected to a darkened compartment by a guillotine door. The floor of the darkened compartment consisted of stainless steel rods through which an electric foot-shock could be delivered from a constant current source. All experimental groups were first habituated to the apparatus the day before the start of the experiment. During the training, the rat (Male Spraque-Dawley (Harlan) weighing 250 to 350 g) was placed in the illuminated compartment facing away from the closed guillotine door for 1 minute before the door was raised. The latency for entering the darkened compartment was recorded. After the rat entered the darkened compartment, the door was closed and a 0.5 mA electric shock was administered for 3 seconds. Twenty-four hours later, the rat was administered 0.1 mg/kg MK-801 or saline, 30 minutes prior to the injection of saline or test compound (dosed from 0.1 to 2.5 mg/kg, i.p.), which was 30 minutes before the retention test started. The rat was again placed in the illuminated compartment with the guillotine door open. The latency for entering the darkened compartment was recorded for up to 180 seconds, at which time the trial was terminated.

All data were analyzed by analyses of variance (ANOVA); individual comparisons were made using Kewman-Keuls tests. Naive rats required less than 30 seconds, on average, to cross from the illuminated compartment to the darkened compartment. However, 24 hours after the electric shock exposure, most rats pretreated with vehicle did not re-enter the darkened compartment; the average latency was increased up to 175 seconds (p<0.001). Pretreatment with MK-801 (0.1 mg/kg) markedly reduced this latency when compared to the vehicle (p<0.001). This amnesic effect of MK-801 is reversed in a statistically significant manner by actual test compounds in a dose-dependent fashion.

EXAMPLE 12

Radial Arm Maze Task in Rats, an in vivo Test for Learning and Memory

The test was performed as previously described (Zhang, H.-T., Crissman, A. M., Dorairaj, N. R., Chandler, L. J., and O'Donnell, J. M., *Neuropsychopharmacology*, 2000, 23, 198-204.). Five days after initial housing, rats (male Spraque-Dawley (Harlan) weighing 250 to 350 g) were placed in the eight-arm radial maze (each arm was 60×10× 12 cm high; the maze was elevated 70 cm above the floor) for acclimation for two days. Rats were then placed individually in the center of the maze for 5 minutes with food pellets placed close to the food wells, and then, the next day, in the wells at the end of the arms; 2 sessions a day were conducted. Next, four randomly selected arms were then baited with one pellet of food each. The rat was restricted to the center platform (26 cm in diameter) for 15 seconds and then allowed to move freely throughout the maze until it collected all pellets of food or 10 minutes passed, whichever came first. Four parameters were recorded: 1) working memory errors, i.e., entries into baited arms that had already been visited during the same trial; 2) reference memory errors, i.e., entries into unbaited arms; 3) total arm entries; and 4) the test duration (seconds), i.e., the time spent in the collection of all the pellets in the maze. If the working memory error was zero and the average reference memory error was less than one in five successive trials, the rats began the drug tests. MK-801 or saline was injected 15 minutes prior to vehicle or test agent, which was given 45 minutes before the test. Experiments were performed in a lighted room, which contained several extra-maze visual cues.

All data were analyzed by analyses of variance (ANOVA); individual comparisons were made using Kewman-Keuls tests. Compared to control, MK-801 (0.1 mg/kg, i.p.) increased the frequencies of both working and reference memory errors (p<0.01). This amnesic effect of MK-801 on working memory is reversed in a statistically significant manner by the administration of actual test compounds in a dose-dependent fashion.

The preceding examples can be repeated with similar success by substituting the generically or specifically described reactants and/or operating conditions of this invention for those used in the preceding examples.

While the invention has been illustrated with respect to the production and of particular compounds, it is apparent that variations and modifications of the invention can be made without departing from the spirit or scope of the invention.

What is claimed is:
1. A compound of Formula I:

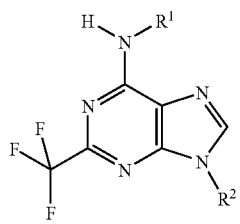

I wherein,
$R^1$ is alkyl having 1 to 5 carbon atoms, which is substituted one or more times by halogen, hydroxy, or combinations thereof, and wherein a —$CH_2$— group can be optionally replaced by —O—, —S—, or —NH—,
cycloalkyl having 3 to 6 carbon atoms, or
cycloalkylalkyl having 4 to 7 carbon atoms; and $R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH═CH— or —C≡C—,
alkoxyalkyl having 3 to 12 carbon atoms,
cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
cycloalkylalkyl having to 12 carbon atoms which is unsubstituted or substituted one or more times by $C_{1-4}$ alkyl, halogenated $C_{1-4}$ alkyl, $C_{1-4}$ alkoxy, cyano, halogen, or combinations thereof,
aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—$NH_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
arylalkyl having 7 to 16 carbon atoms, which is substituted one or more times by halogen, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—$NH_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—$NH_2$, $C_{1-4}$-alkylthio, $C_{1-4}$-alkylsulphinyl, $C_{1-4}$-alkylsulphonyl, or combinations thereof,
heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—$NH_2$, $C_{1-4}$-alkylthio, $C_{1-4}$-alkylsulphinyl, $C_{1-4}$-alkylsulphonyl, or combinations thereof,
heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof;
heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, oxo, amino, C$_{1-4}$-alkylamino, di-C$_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof; and pharmaceutically acceptable salts thereof,
with the proviso that when R$^1$ is cyclopropyl, then R$^2$ is not cyclopropylmethyl, or cyclopropylethyl.

2. A compound according to claim 1, wherein R$^1$ is substituted alkyl.

3. A compound according to claim 1, wherein R$^1$ is cycloalkyl.

4. A compound according to claim 1, wherein R$^1$ is cycloalkylalkyl.

5. A compound according to claim 1, wherein R$^2$ is substituted or unsubstituted alkyl.

6. A compound according to claim 1, wherein R$^2$ is alkoxyalkyl.

7. A compound according to claim 1, wherein R$^2$ is substituted or unsubstituted cycloalkyl.

8. A compound according to claim 1, wherein R$^2$ is substituted or unsubstituted aryl.

9. A compound according to claim 1, wherein R$^2$ is substituted or unsubstituted arylalkyl.

10. A compound according to claim 1, wherein R$^2$ is substituted or unsubstituted heteroaryl.

11. A compound according to claim 1, wherein R$^2$ is substituted or unsubstituted heteroarylalkyl.

12. A compound according to claim 1, wherein R$^2$ is substituted or unsubstituted heterocycle.

13. A compound according to claim 1, wherein R$^2$ is substituted or unsubstituted heterocycle-alkyl.

14. A compound according to claim 1, wherein R$^2$ is substituted or unsubstituted carbocycle.

15. A compound according to claim 1, wherein R$^1$ is cycloalkyl or cycloalkylalkyl.

16. A compound according to claim 5, wherein R$^1$ is cycloalkyl or cycloalkylalkyl.

17. A compound according to claim 6, wherein R$^1$ is cycloalkyl or cycloalkylalkyl.

18. A compound according to claim 7, wherein R$^1$ is cycloalkyl or cycloalkylalkyl.

19. A compound according to claim 8, wherein R$^1$ is cycloalkyl or cycloalkylalkyl.

20. A compound according to claim 9, wherein R$^1$ is cycloalkyl or cycloalkylalkyl.

21. A compound according to claim 10, wherein R$^1$ is cycloalkyl or cycloalkylalkyl.

22. A compound according to claim 11, wherein R$^1$ is cycloalkyl or cycloalkylalkyl.

23. A compound according to claim 12, wherein R$^1$ is cycloalkyl or cycloalkylalkyl.

24. A compound according to claim 13, wherein R$^1$ is cycloalkyl or cycloalkylalkyl.

25. A compound according to claim 14, wherein R$^1$ is cycloalkyl or cycloalkylalkyl.

26. A compound according to claim 1, wherein R$^1$ is cyclopropyl, cyclopentyl, or cyclopropylmethyl.

27. A compound according to claim 1, wherein R$^1$ is cyclopropyl, cyclobutyl, cyclopentyl or cyclohexyl.

28. A compound according to claim 1, wherein R$^1$ is cyclopropyl.

29. A compound according to claim 1, wherein R$^2$ is alkyl, arylalkyl, cycloalkyl, aryl, heteroaryl, heteroarylalkyl, or alkoxyalkyl.

30. A compound according to claim 1, wherein R$^2$ is ethyl, isopropyl, butyl, tert-butyl, cyclopentyl, cyclohexyl, cycloheptyl, or arylalkyl which is unsubstituted or substituted one or more times by F, Cl, CN, CF$_3$, CH$_3$, C$_2$H$_5$, isopropyl, OCH$_3$, methylenedioxy, ethylenedioxy or combinations thereof.

31. A compound according to claim 1, wherein R$^2$ is substituted or unsubstituted benzyl, phenethyl or phenpropyl.

32. A compound of formula II

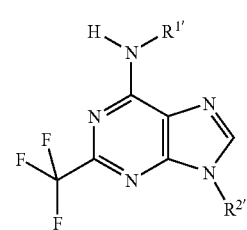

wherein

R$^{1'}$ is methyl, ethyl, or cyclopropyl; and

R$^{2'}$ is cycloalkyl having 3 to 12 carbon atoms, which is unsubstituted or substituted one or more times by halogen, C$_{1-4}$ alkyl, halogenated C$_{1-4}$ alkyl, C$_{1-4}$ alkoxy, cyano or combinations thereof, aryl having 6 to 14 carbon atoms, which is unsubstituted or substituted one or more times by halogen, C$_{1-4}$ alkyl, halogenated C$_{1-4}$ alkyl, hydroxy, C$_{1-4}$-alkoxy, halogenated C$_{1-4}$ alkoxy, nitro, methylenedioxy, ethylenedioxy, amino, C$_{1-4}$ alkylamino, di-C$_{1-4}$-alkylamino, C$_{1-4}$-hydroxyalkyl, C$_{1-4}$-hydroxyalkoxy, carboxy, cyano, —C(O)—NHOH, —C(O)—NH$_2$, C$_{2-4}$-acyl, C$_{2-4}$-alkoxycarbonyl, C$_{1-4}$-alkylthio, C$_{1-4}$-alkylsulphinyl, C$_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, amino, C$_{1-4}$-alkylamino, di-C$_{1-4}$-alkylamino, carboxy, alkoxycarbonyl, —C(O)—NHOH, —C(O)—NH$_2$, C$_{1-4}$-alkylthio, C$_{1-4}$-alkylsulphinyl, C$_{1-4}$-alkylsulphonyl, or combinations thereof, heterocycle having 5 to 10 ring atoms in which at least 1 ring atom is a heteroatom, which is unsubstituted or is substituted one or more times by halogen, aryl, C$_{1-4}$ alkyl, halogenated C$_{1-4}$ alkyl, hydroxy, C$_{1-4}$-alkoxy, halogenated C$_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof; and pharmaceutically acceptable salts thereof.

33. A compound of Formula III:

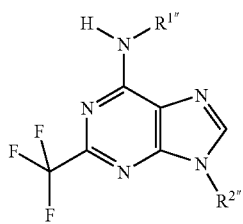

III wherein $R^{1''}$ is methyl, ethyl, or cyclopropyl; and $R^{2''}$ is phenyl, phenyl which is substituted one or more times by halogen, $C_{1-4}$ alkyl, halogenated $C_{1-4}$ alkyl, hydroxy, $C_{1-4}$-alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, or heteroaryl having 5 to 10 ring atoms in which at least 1 ring atom is a heteroatom, substituted heteroaryl having 5 to 10 ring atoms, in which at least 1 ring atom is a heteroatom, which is unsubstituted or substituted one or more times by halogen, aryl, $C_{1-4}$-alkyl, $C_{1-4}$-alkoxy, cyano, trifluoromethyl, nitro, amino, $C_{1-4}$-alkylamino, di-$C_{1-4}$-alkylamino or combinations thereof, or when $R^1$ is methyl or cyclopropyl $R^2$ can also be cycloalkyl having 3 to 12 carbon atoms; and pharmaceutically acceptable salts thereof.

34. A compound selected from:

6-Cyclopropylamino-9-(2-fluorobenzyl)-2-trifluoromethylpurine
6-Cyclopropylamino-9-(4-fluorobenzyl)-2-trifluoromethylpurine
6-Cyclopropylamino-9-(2,6-difluorobenzyl)-2-trifluoromethylpurine
6-Cyclopropylamino-9-(2,3-difluorobenzyl)-2-trifluoromethylpurine
6-Cyclopropylamino-9-propyl-2-trifluoromethylpurine
6-Cyclopropylamino-9-cyclopentyl-2-trifluoromethylpurine
6-Cyclopropylamino-9-(3,4-dimethoxybenzyl)-2-trifluoromethylpurine
6-Cyclopropylamino-9-(3,4-methylenedioxybenzyl)-2-trifluoromethylpurine
6-Cyclopropylamino-9-(3-thiophenemethyl)-2-trifluoromethylpurine
6-Cyclopropylamino-9-cycloheptyl-2-trifluoromethylpurine
6-Methylamino-9-cyclopentyl-2-trifluoromethylpurine
6-Cyclopropylamino-9-cyclohexyl-2-trifluoromethylpurine
6-Methylamino-9-cycloheptyl-2-trifluoromethylpurine
6-Cyclopropylamino-9-cyclopentylmethyl-2-trifluoromethylpurine
6-Cyclopropylamino-9-phenyl-2-trifluoromethylpurine
6-Cyclopropylamino-9-(2-fluorophenyl)-2-trifluoromethylpurine
6-Cyclopropylamino-9-cyclobutyl-2-trifluoromethylpurine
6-Cyclopropylamino-9-(2-norboranane)-2-trifluoromethylpurine
6-Cyclopropylamino-9-(1-indanyl)-2-trifluoromethylpurine
6-Cyclopropylamino-9-(4-fluorophenyl)-2-trifluoromethylpurine
6-Cyclopropylamino-9-(4-chlorophenyl)-2-trifluoromethylpurine
6-Cyclopropylamino-9-(3-thienyl)-2-trifluoromethylpurine
6-Cyclopropylamino-9-(3-cyclopentyloxy-4-methoxybenzyl)-2-trifluoromethylpurine
6-Cyclopropylamino-9-(3,4-dimethoxyphenyl)-2-trifluoromethylpurine
6-Cyclopropylamino-9-(2,6-dichloro-4-pyridylmethyl)-2-trifluoromethylpurine
6-Cyclopropylamino-9-(4-methoxybenzyl)-2-trifluoromethylpurine
6-Cyclopropylamino-9-(3-methoxyphenyl)-2-trifluoromethylpurine
6-Cyclopropylamino-9-(4-methoxyphenyl)-2-trifluoromethylpurine
6-Cyclopropylamino-9-(3-nitrophenyl)-2-trifluoromethylpurine
6-Cyclopropylamino-9-(2-methoxyphenyl)-2-trifluoromethylpurine
6-Cyclopropylamino-9-(3-cyanophenyl)-2-trifluoromethylpurine
6-Cyclopropylamino-9-(2,4-dimethoxyphenyl)-2-trifluoromethylpurine
6-Cyclopropylamino-9-(3-nitrobenzyl)-2-trifluoromethylpurine
6-Cyclopropylamino-9-(6-methoxy-3-pyridyl)-2-trifluoromethylpurine
6-Cyclopropylamino-9-(4-pyridyl)-2-trifluoromethylpurine
6-Cyclopropylamino-9-(3-pyridyl)-2-trifluoromethylpurine
6-Cyclopropylamino-9-(4-dimethylaminophenyl)-2-trifluoromethylpurine
6-Cyclopropylamino-9-(3-aminophenyl)-2-trifluoromethylpurine
6-Methylamino-9-(2,4-dimethoxy-5-pyrimidyl)-2-trifluoromethylpurine
6-Methylamino-9-(2-methoxyphenyl)-2-trifluoromethylpurine
6-Methylamino-9-(4-methoxyphenyl)-2-trifluoromethylpurine
6-Methylamino-9-(3-acetylphenyl)-2-trifluoromethylpurine
6-Methylamino-9-(3-methoxyphenyl)-2-trifluoromethylpurine 6-Methylamino-9-(3-nitrophenyl)-2-trifluoromethylpurine
6-Cyclopropylamino-9-(3-furanyl)-2-trifluoromethylpurine
6-Cyclopropylamino-9-(4-ethoxyphenyl)-2-trifluoromethylpurine
6-Cyclopropylamino-9-(2-ethoxyphenyl)-2-trifluoromethylpurine
6-Cyclopropylamino-9-(3,4-methylenedioxyphenyl)-2-trifluoromethylpurine
6-Cyclopropylamino-9-(3-ethoxyphenyl)-2-trifluoromethylpurine
6-Methylamino-9-(3,4-dimethoxyphenyl)-2-trifluoromethylpurine; and pharmaceutically acceptable salts thereof.

35. A compound according to claim 34, wherein said compound is selected from:
6-Cyclopropylamino-9-(2,3-difluorobenzyl)-2-trifluoromethylpurine
6-Cyclopropylamino-9-cyclopentyl-2-trifluoromethylpurine
6-Cyclopropylamino-9-(3,4-dimethoxybenzyl)-2-trifluoromethylpurine
6-Cyclopropylamino-9-cycloheptyl-2-trifluoromethylpurine
6-Methylamino-9-cyclopentyl-2-trifluoromethylpurine
6-Cyclopropylamino-9-cyclohexyl-2-trifluoromethylpurine
6-Methylamino-9-cycloheptyl-2-trifluoromethylpurine
6-Cyclopropylamino-9-phenyl-2-trifluoromethylpurine
6-Cyclopropylamino-9-(2-fluorophenyl)-2-trifluoromethylpurine
6-Cyclopropylamino-9-cyclobutyl-2-trifluoromethylpurine
6-Cyclopropylamino-9-(2-norboranane)-2-trifluoromethylpurine
6-Cyclopropylamino-9-(4-fluorophenyl)-2-trifluoromethylpurine
6-Cyclopropylamino-9-(4-chlorophenyl)-2-trifluoromethylpurine
6-Cyclopropylamino-9-(3-thienyl)-2-trifluoromethylpurine
6-Cyclopropylamino-9-(3,4-dimethoxyphenyl)-2-trifluoromethylpurine
6-Cyclopropylamino-9-(2,6-dichloro-4-pyridylmethyl)-2-trifluoromethylpurine
6-Cyclopropylamino-9-(4-methoxybenzyl)-2-trifluoromethylpurine
6-Cyclopropylamino-9-(3-methoxyphenyl)-2-trifluoromethylpurine
6-Cyclopropylamino-9-(4-methoxyphenyl)-2-trifluoromethylpurine
6-Cyclopropylamino-9-(3-nitrophenyl)-2-trifluoromethylpurine
6-Cyclopropylamino-9-(2-methoxyphenyl)-2-trifluoromethylpurine
6-Cyclopropylamino-9-(3-cyanophenyl)-2-trifluoromethylpurine
6-Cyclopropylamino-9-(3-nitrobenzyl)-2-trifluoromethylpurine
6-Cyclopropylamino-9-(4-pyridyl)-2-trifluoromethylpurine
6-Methylamino-9-(2,4-dimethoxy-5-pyrimidyl)-2-trifluoromethylpurine
6-Methylamino-9-(4-methoxyphenyl)-2-trifluoromethylpurine
6-Methylamino-9-(3-acetylphenyl)-2-trifluoromethylpurine
6-Methylamino-9-(3-methoxyphenyl)-2-trifluoromethylpurine
6-Methylamino-9-(3-nitrophenyl)-2-trifluoromethylpurine
6-Cyclopropylamino-9-(3-ethoxyphenyl)-2-trifluoromethylpurine
6-Methylamino-9-(3,4-dimethoxyphenyl)-2-trifluoromethylpurine; and pharmaceutically acceptable salts thereof.

36. A pharmaceutical composition comprising a compound according to claim 1 and a pharmaceutically acceptable carrier.

37. A composition according to claim 36, wherein said composition contains 0.1-50 mg of said compound.

38. A process for preparing compounds of the formula IV

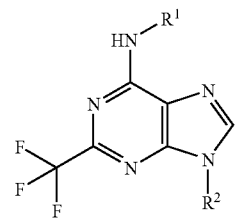

wherein
$R^1$ is H,
alkyl having 1 to 5 carbon atoms, which is unsustituted or substituted one or more times by halogen, hydroxy, or combinations thereof, and wherein a —CH$_2$— group can be optionally replaced by —O—, —S—, or —NH—,
cycloalkyl having 3 to 6 carbon atoms, or
cycloalkylalkyl having 4 to 7 carbon atoms; and
$R^2$ is aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof,
said process comprising:
reacting 6-N-$R^1$-2-CF-substituted adenine with an arylboronic acid or heteroarylboronic acid in the presence of trialkylamine wherein the alkyl portions each have 1 to 5 carbon atoms as a base, a copper catalyst, and a polar aprotic solvent, at a temperature of at least 50° C.

39. A compound according to claim 1, wherein $R^2$ is cycloalkylalkyl.

40. A compound according to claim 39, wherein $R^1$ is cycloalkyl or cycloalkylalkyl.

41. A compound according to claim 1, wherein said compound is 6-cyclopropylamino-9-(2-methoxyphenyl)-2-trifluoromethylpurine, or a pharmaceutically acceptable salt thereof.

42. A compound according to claim 1, wherein said compound is 6-cyclopropylamino-9-(2-fluorobenzyl)-2-trifluoromethylpurine, or a pharmaceutically acceptable salt thereof.

43. A compound according to claim 1, wherein $R^1$ is cycloalkyl and $R^2$ is phenyl or heteroaryl, in each case substituted or unsubstituted.

44. A compound according to claim 1, wherein
$R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
alkoxyalkyl having 3 to 12 carbon atoms,
cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
cycloalkylalkyl having 4 to 12 carbon atoms, which is unsubstituted or substituted one or more times by $C_{1-4}$ alkyl, halogenated $C_{1-4}$ alkyl, $C_{1-4}$ alkoxy, cyano, halogen, or combinations thereof,
aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
arylalkyl having 7 to 16 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$— alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, $C_{1-4}$-alkylthio, $C_{1-4}$-alkylsulphinyl, $C_{1-4}$-alkylsulphonyl, or combinations thereof,
heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, $C_{1-4}$-alkylthio, $C_{1-4}$-alkylsulphinyl, $C_{1-4}$-alkylsulphonyl, or combinations thereof,
heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof;
heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or
carbocycle which is a nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

45. A compound according to claim 32, wherein
$R^{2'}$ is cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof,
heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, $C_{1-4}$-alkylthio, $C_{1-4}$-alkylsulphinyl, $C_{1-4}$-alkylsulphonyl, or combinations thereof,
heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or
carbocycle which is a nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

46. A compound according to claim 33, wherein $R^{2''}$ isphenyl,
   phenyl which is substituted one or more times by halogen, $C_{1-4}$ alkyl, halogenated $C_{1-4}$ alkyl, hydroxy, $C_{1-4}$-alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, or
   heteroaryl having 5 to 10 ring atoms in which at least 1 ring atom is a heteroatom, substituted heteroaryl having 5 to 10 ring atoms, in which at least 1 ring atom is a heteroatom, which is unsubstituted or substituted one or more times by halogen, aryl, $C_{1-4}$-alkyl, $C_{1-4}$-alkoxy, cyano, trifluoromethyl, nitro, amino, $C_{1-4}$-alkylamino, di-$C_{1-4}$-alkylamino or combinations thereof.

47. A compound according to claim 1, wherein
    $R^1$ is cyclopropyl; and
    $R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
    cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
    cycloalkylalkyl having 4 to 12 carbon atoms, which is unsubstituted or substituted one or more times by $C_{1-4}$ alkyl, halogenated $C_{1-4}$ alkyl, $C_{1-4}$ alkoxy, cyano, halogen, or combinations thereof,
    aryl having 6 to 14 carbon atoms, which is unsubstituted or substituted one or more times by halogen, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, or combinations thereof,
    arylalkyl having 7 to 16 carbon atoms, which is unsubstituted or substituted one or more times by halogen, halogenated $C_{1-4}$ alkyl, hydroxy, $C_{1-4}$-alkoxy, halogenated $C_{1-4}$ alkoxy, nitro, methylenedioxy, ethylenedioxy, or combinations thereof,
    heteroaryl having 5 to 10 ring atoms in which at least 1 ring atom is a heteroatom, which is unsubstituted or substituted one or more times by halogen, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, $C_{1-4}$-alkylthio, $C_{1-4}$-alkylsulphinyl, $C_{1-4}$-alkylsulphonyl, or combinations thereof,
    heteroarylalkyl wherein the heteroaryl portion has 5 to 10 ring atoms in which at least 1 ring atom is a heteroatom and the alkyl portion has 1 to 3 carbon atoms, the heteroaryl portion is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, $C_{1-4}$-alkylthio, $C_{1-4}$-alkylsulphinyl, $C_{1-4}$-alkylsulphonyl, or combinations thereof,
    heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof;
    heterocycle-alkyl wherein the heterocycle portion has 5 to 10 ring atoms in which
    at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or
    carbocycle which is a nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-alkanoyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

48. A compound according to claim 33, wherein
    $R^{2''}$ is phenyl, or
    phenyl which is substituted one or more times by halogen, $C_{1-4}$ alkyl, halogenated $C_{1-4}$ alkyl, hydroxy, $C_{1-4}$-alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

49. A compound according to claim 1, wherein when $R^1$ is cyclopropyl, $R^2$ is not cycloalkylalkyl.

50. A compound according to claim 1, wherein
    $R^2$ is alkyl having 1 to 12 carbon atoms, which is unsubstituted or substituted one or more times by halogen, hydroxy, cyano or combinations thereof, wherein one or more —$CH_2$— groups is each independently optionally replaced by —O—, —S—, or —NH—, and wherein optionally one or more —$CH_2CH_2$— groups is replaced in each case by —CH=CH— or —C≡C—,
    alkoxyalkyl having 3 to 12 carbon atoms,
    cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof,
    cycloalkylalkyl having 4 to 12 carbon atoms, which is unsubstituted or substituted one or more times by $C_{1-4}$ alkyl, halogenated $C_{1-4}$ alkyl, $C_{1-4}$ alkoxy, cyano, halogen, or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, arylalkyl having 7 to 16 carbon atoms, which is substituted one or more times by halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, and the heteroaryl portion is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

51. A compound according to claim 49, wherein $R^2$ is alkyl having 1 to 12 carbon atoms, which is unsubstituted or substituted one or more times by halogen, hydroxy, cyano or combinations thereof, wherein one or more —CH$_2$— groups is each independently optionally replaced by —O—, —S—, or —NH—, and wherein optionally one or more —CH$_2$CH$_2$— groups is replaced in each case by —CH=CH— or —C≡C—, alkoxyalkyl having 3 to 12 carbon atoms, cycloalkyl having 3 to 12 carbon atoms, which is unsubstituted or substituted one or more times by halogen, $C_{1-4}$ alkyl, halogenated $C_{1-4}$ alkyl, $C_{1-4}$ alkoxy, cyano or combinations thereof, cycloalkylalkyl having 4 to 12 carbon atoms, which is unsubstituted or substituted one or more times by $C_{1-4}$ alkyl, halogenated $C_{1-4}$ alkyl, $C_{1-4}$ alkoxy, cyano, halogen, or combinations thereof, aryl having 6 to 14 carbon atoms, which is unsubstituted or substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, arylalkyl having 7 to 16 carbon atoms, which is substituted one or more times by halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof, heteroaryl having 5 to 10 ring atoms in which at least 1 ring atom is a heteroatom, which is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof, heteroarylalkyl wherein the heteroaryl portion has 5 to 10 ring atoms in which at least 1 ring atom is a heteroatom and the alkyl portion has 1 to 3 carbon atoms, and the heteroaryl portion is unsubstituted or substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, amino, $C_{1-4}$-alkylamino, di-$C_{1-4}$-alkylamino, carboxy, alkoxycarbonyl, —C(O)—NHOH, —C(O)—NH$_2$, $C_{1-4}$-alkylthio, $C_{1-4}$-alkylsulphinyl, $C_{1-4}$-alkylsulphonyl, or combinations thereof, heterocycle having 5 to 10 ring atoms in which at least 1 ring atom is a heteroatom, which is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, heterocycle-alkyl wherein the heterocycle portion has 5 to 10 ring atoms in which at least 1 ring atom is a heteroatom and the alkyl portion has 1 to 3 carbon atoms, the heterocycle portion is nonaromatic and is unsubstituted or is substituted one or more times by halogen, aryl, $C_{1-4}$ alkyl, halogenated $C_{1-4}$ alkyl, hydroxy, $C_{1-4}$-alkoxy, halogenated $C_{1-4}$ alkoxy, cyano, trifluoromethyl, nitro, oxo, amino, $C_{1-4}$-alkylamino, di-$C_{1-4}$-alkylamino, carboxy, alkoxycarbonyl, or combinations thereof, or carbocycle which is nonaromatic, monocyclic or bicyclic, group having 5 to 14 carbon atoms, which is unsubstituted or is substituted one or more times by halogen, $C_{1-4}$ alkyl, halogenated $C_{1-4}$ alkyl, hydroxy, $C_{1-4}$-alkoxy, halogenated $C_{1-4}$ alkoxy, nitro, methylenedioxy, ethylenedioxy, amino, $C_{1-4}$ alkylamino, di-$C_{1-4}$-alkylamino, $C_{1-4}$-hydroxyalkyl, $C_{1-4}$-hydroxyalkoxy, carboxy, cyano, —C(O)—NHOH, —C(O)—NH$_2$, $C_{2-4}$-acyl, $C_{2-4}$-alkoxycarbonyl, $C_{1-4}$-alkylthio, $C_{1-4}$-alkylsulphinyl, $C_{1-4}$-alkylsulphonyl, phenoxy, or combinations thereof.

52. A compound according to claim 1, wherein when $R^1$ is cyclopropyl, $R^2$ is not arylalkyl.

53. A compound according to claim 49, wherein when $R^1$ is cyclopropyl, $R^2$ is not arylalkyl.

54. A compound according to claim 50, wherein when $R^1$ is cyclopropyl, $R^2$ is not arylalkyl.

55. A compound according to claim 51, wherein when $R^1$ is cyclopropyl, $R^2$ is not arylalkyl.

56. A compound according to claim 1, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

57. A compound according to claim 49, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

58. A compound according to claim 50, wherein $R^1$ is cycloalkyl having 3 to 6 carbon atoms, or cycloalkylalkyl having 4 to 7 carbon atoms.

59. A compound according to claim 51, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

60. A compound according to claim 52, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

61. A compound according to claim 53, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

62. A compound according to claim 54, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

63. A compound according to claim 55, wherein
$R^1$ is alkyl having 1 to 5 carbon atoms, which is substituted one or more times by halogen, hydroxy, or combinations thereof,
cycloalkyl having 3 to 6 carbon atoms, or
cycloalkylalkyl having 4 to 7 carbon atoms.

64. A pharmaceutical composition comprising a compound according to claim 32 and a pharmaceutically acceptable carrier.

65. A pharmaceutical composition comprising a compound according to claim 33 and a pharmaceutically acceptable carrier.

66. A pharmaceutical composition comprising a compound according to claim 34 and a pharmaceutically acceptable carrier.

67. A pharmaceutical composition comprising a compound according to claim 35 and a pharmaceutically acceptable carrier.

68. A compound according to claim 1, wherein $R^2$ is cycloalkylalkyl wherein the cycloalkyl portion is cyclobutyl, cyclopentyl, cyclohexyl, cycloheptyl, cyclooctyl, cyclononyl, norbornyl, 1-decalin, adamant-1-yl, or adamant-2-yl.

* * * * *